(12) United States Patent
Yen et al.

(10) Patent No.: US 9,190,619 B2
(45) Date of Patent: Nov. 17, 2015

(54) COMPOUND FOR ORGANIC ELECTROLUMINESCENCE DEVICE

(71) Applicant: LUMINESCENCE TECHNOLOGY CORPORATION, Hsin-Chu (TW)

(72) Inventors: Feng-Wen Yen, Taipei (TW); Cheng-Hao Chang, Miao-Li (TW)

(*) Notice: Subject to any disclaimer, the term of this patent is extended or adjusted under 35 U.S.C. 154(b) by 0 days.

(21) Appl. No.: 14/591,006

(22) Filed: Jan. 7, 2015

(65) Prior Publication Data

US 2015/0214492 A1 Jul. 30, 2015

Related U.S. Application Data

(63) Continuation-in-part of application No. 13/716,216, filed on Dec. 17, 2012, now Pat. No. 8,993,130.

(51) Int. Cl.
| | |
|---|---|
| *H01L 51/50* | (2006.01) |
| *H01L 51/00* | (2006.01) |
| *C07D 403/04* | (2006.01) |
| *C07D 209/94* | (2006.01) |
| *C09K 11/06* | (2006.01) |
| *H01L 51/52* | (2006.01) |

(52) U.S. Cl.
CPC .......... *H01L 51/0072* (2013.01); *C07D 209/94* (2013.01); *C07D 403/04* (2013.01); *C09K 11/06* (2013.01); *H01L 51/0058* (2013.01); *H01L 51/0067* (2013.01); *H01L 51/0073* (2013.01); *H01L 51/0074* (2013.01); *C09K 2211/1011* (2013.01); *H01L 51/0054* (2013.01); *H01L 51/0056* (2013.01); *H01L 51/0085* (2013.01); *H01L 51/5004* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01); *H01L 2251/301* (2013.01); *H01L 2251/308* (2013.01); *Y10S 428/917* (2013.01)

(58) Field of Classification Search
None
See application file for complete search history.

(56) References Cited

U.S. PATENT DOCUMENTS

2013/0048975 A1* 2/2013 Hong .................. C07D 209/80
257/40
2014/0231754 A1 8/2014 Yen

*Primary Examiner* — Gregory Clark

(57) ABSTRACT

The present invention discloses a compound is represented by the following formula (I) or formula (II), the organic EL device employing the compound as phosphorescent host material, hole blocking material, hole blocking electron transport material, can display good performance.

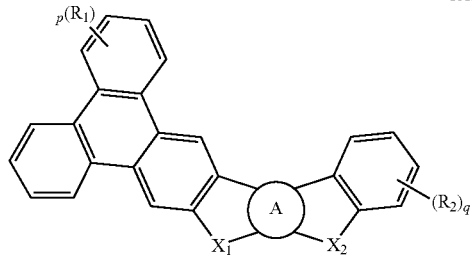

formula(I)

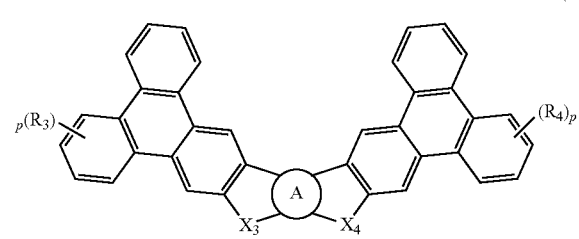

formula(II)

The same definition as described in the present invention.

15 Claims, 1 Drawing Sheet

| | |
|---|---|
| 13 | — metal electrode |
| 12 | — electron injection layer |
| 11 | — electron transport layer |
| 10 | — hole blocking layer |
| 9 | — emitting layer |
| 8 | — hole transport layer |
| 7 | — hole injection layer |
| 6 | — transparent electrode |

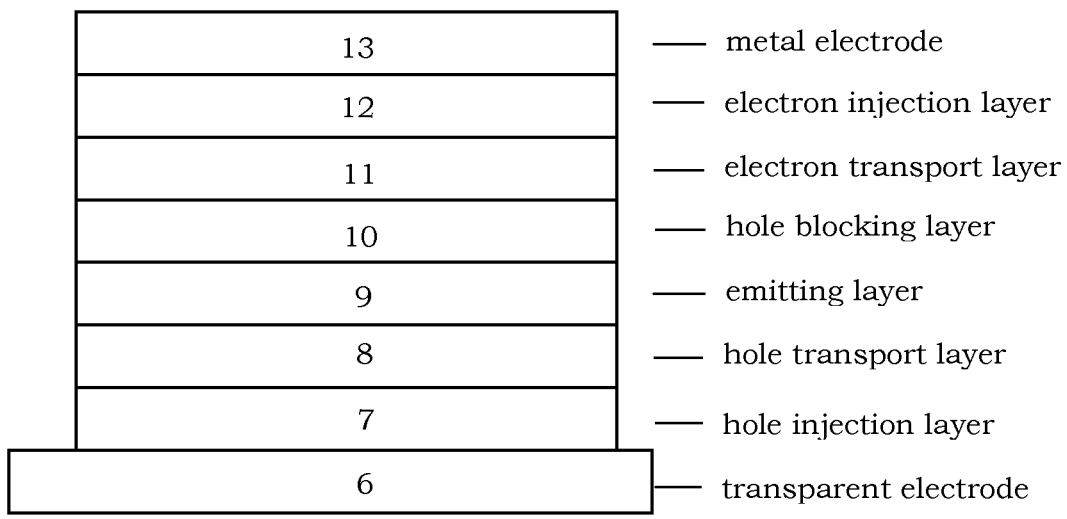

COMPOUND FOR ORGANIC ELECTROLUMINESCENCE DEVICE

This application is a Continuation-in-Part of U.S. patent Ser. No. 13/716,216, filed Dec. 17, 2012.

FIELD OF INVENTION

The present invention generally relates to a compound and organic electroluminescent (herein referred to as organic EL) device using the compound. More specifically, the present invention relates to the compound having general formula (I) or formula (II), an organic EL device employing the compound as phosphorescent emitting host, hole blocking layer (HBL) or hole blocking electron transport layer (HBETL).

BACKGROUND OF THE INVENTION

Organic electroluminescent (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, Thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%.

Recently, a new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the siglet level by the mechanism of reverse inter-system crossing (RISC).

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or the electron transporting layer with hole blocking ability instead of typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO (highest occupied molecular orbital) and LUMO (lowest unoccupied molecular orbital) energy levels suitable to block hole transport from the EML to the ETL and to pass electrons from the ETL to the EML, in addition, the good thermal and electrochemical stability of the phosphorescent emitting host material are also needed.

There continues to be a need for organic EL materials which is able to efficiently transport electrons or holes and block holes, with good thermal stability and more efficient EML material for high emitting efficiency. According to the reasons described above, the present invention has the objective of resolving such problems of the prior-art and offering a light emitting device which is excellent in its thermal stability, high luminance efficiency, high luminance and long half-life time. The present invention disclose a material having general formula (I) or formula (II), used as phosphorescent emitting host, hole blocking layer (HBL) or hole blocking electron transport layer (HBETL) have good charge carrier mobility and excellent operational durability can lower driving voltage and power consumption, increasing efficiency and half-life time of organic EL device.

SUMMARY OF THE INVENTION

Provided a compound can use as phosphorescent emitting host, hole blocking layer or hole blocking electron transport layer for organic EL device. The compound can overcome the drawbacks of the conventional materials like as lower efficiency, half-lifetime and higher power consumption.

An object of the present invention is to provide the compound which can be used as phosphorescent emitting host, hole blocking layer or hole blocking electron transport layer for organic EL device.

The present invention has the economic advantages for industrial practice. Accordingly the present invention, the compound which can be used for organic EL device is disclosed. The mentioned the compound is represented by the following formula (I) or formula (II)

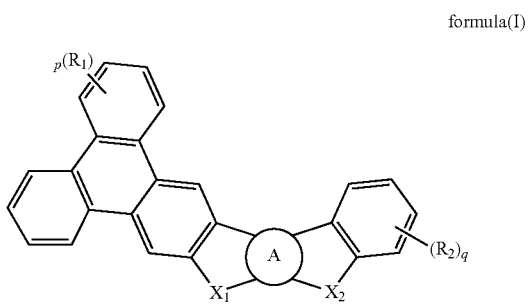

formula(I)

formula(II)

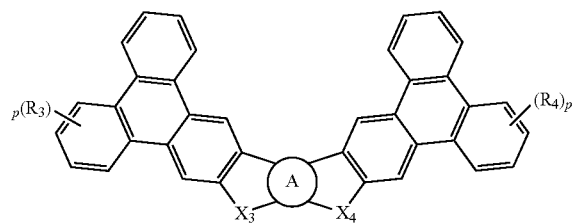

Wherein A represent a substituted or unsubstituted phenyl group, a substituted or unsubstituted naphthyl group. $X_1$ to $X_4$ independently represent a divalent bridge selected from the atom or group consisting from O, S, $C(R_5)(R_6)$, N(Ar), $Si(R_7)(R_8)$. p represent an integer of 0 to 10. q represent an integer of 0 to 4. $R_1$ to $R_8$, and Ar independently selected from the group consisting of a hydrogen atom, a substituted or unsubstituted alkyl group having 1 to 30 carbon atoms, a substituted or unsubstituted aryl group having 6 to 50 carbon atoms, a substituted or unsubstituted aralkyl group having 6 to 50 carbon atoms, a substituted or unsubstituted heteroaryl group having 3 to 50 carbon atoms.

BRIEF DESCRIPTION OF THE DRAWINGS

FIG. 1 show one example of organic EL device in the present invention. 6 is transparent electrode, 13 is metal electrode, 7 is hole injection layer which is deposited onto 6, 8 is hole transport layer which is deposited onto 7, 9 is fluorescent or phosphorescent emitting layer which is deposited onto 8, 10 is hole blocking layer which is deposited onto 9, 11 is electron transport layer which is deposited onto 10, 12 is electron injection layer which is deposited on to 11.

DESCRIPTION OF THE PREFERRED EMBODIMENTS

What probed into the invention is the compound and organic EL device using the compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the compound which can be used as phosphorescent emitting host, hole blocking layer or hole blocking electron transport layer for organic EL device are disclosed. The mentioned material are represented by the following formula (I) or formula (II):

formula(I)

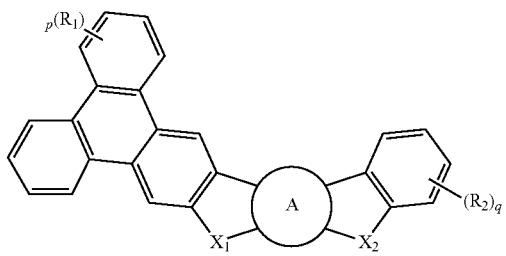

formula(II)

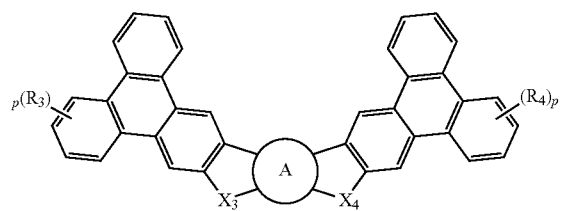

Wherein A represent a substituted or unsubstituted phenyl, a substituted or a unsubstituted naphthyl group. $X_1$ to $X_4$ independently represent a divalent bridge selected from the atom or group consisting from O, S, $C(R_5)(R_6)$, N(Ar), $Si(R_7)(R_8)$. p represent an integer of 0 to 10. q represent an integer of 0 to 4. $R_1$ to $R_8$, and Ar independently selected from the group consisting of a hydrogen atom, a substituted or unsubstituted alkyl group having 1 to 30 carbon atoms, a substituted or unsubstituted aryl group having 6 to 50 carbon atoms, a substituted or unsubstituted aralkyl group having 6 to 50 carbon atoms, a substituted or unsubstituted heteroaryl group having 3 to 50 carbon atoms.

The compound according to the above-mentioned formula (I) or formula (II), wherein the compound is represented the following formula (I-1) to formula (I-4) or formula (II-1) to formula (II-4):

formula(I-1)

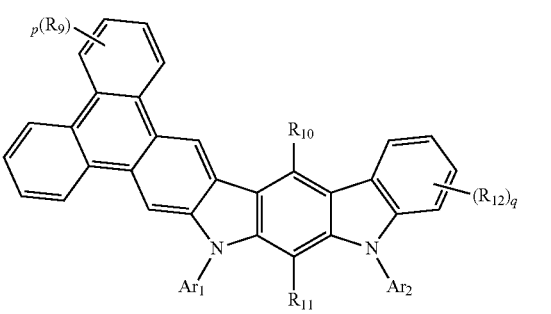

formula(I-2)

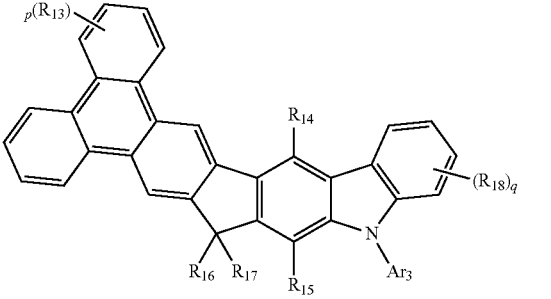

-continued

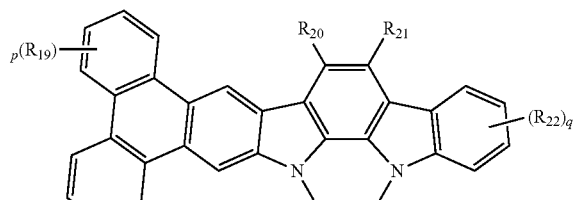
formula(I-3)

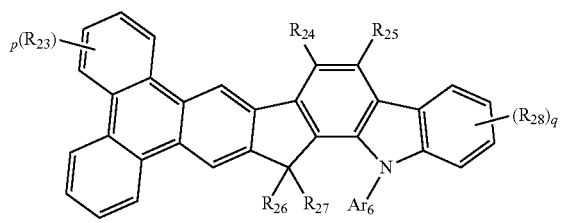
formula(I-4)

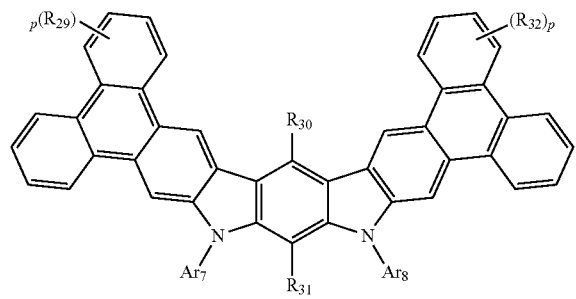
formula(II-1)

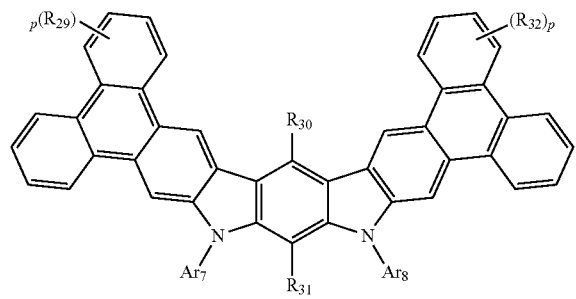
formula(II-2)

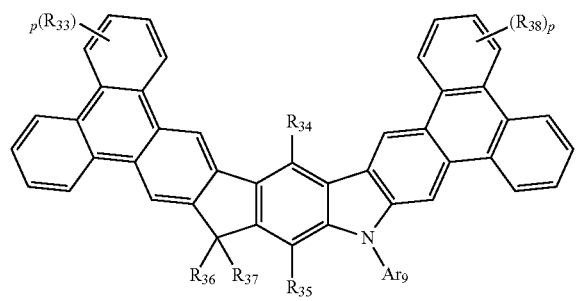
formula(II-3)

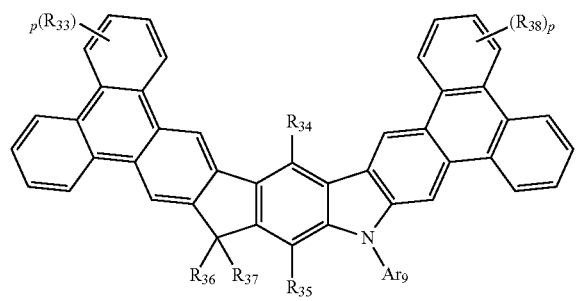
formula(II-4)

wherein $R_9$ to $R_{48}$ are the same definition as $R_1$, and p, q are same definition as described the above-mentioned formula (I) and formula (II), $Ar_1$ to $Ar_{12}$ is represented by the following formula (III):

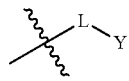
formula(III)

wherein L represent a single bond, a substituted or unsubstituted arylene group having 6 to 30 ring carbon atoms, or a substituted or unsubstituted heterarylene group having 3 to 30 ring carbon atoms. Y represent a substituted or unsubstituted phenyl group, a substituted or unsubstituted naphthyl group, a substituted or unsubstituted biphenyl group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted phenanthroline group, a substituted or unsubstituted dihydroacridine group, a substituted or unsubstituted phenothiazine group, a substituted or unsubstituted phenoxazine group, a substituted or unsubstituted dihydrophenazine group According to the above-mentioned formula (III) for L are consisting of group represent as following:

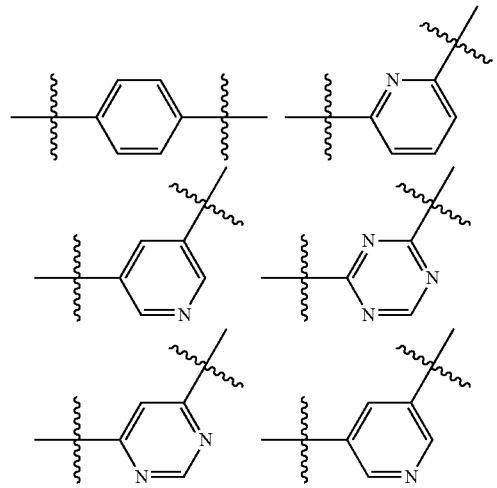

According to the above-mentioned formula (III) for Y are consisting of group represent as following:

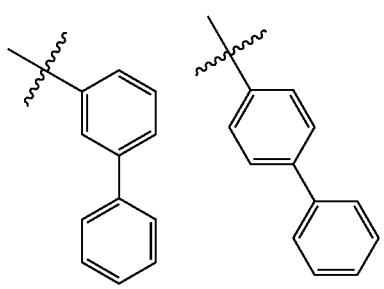

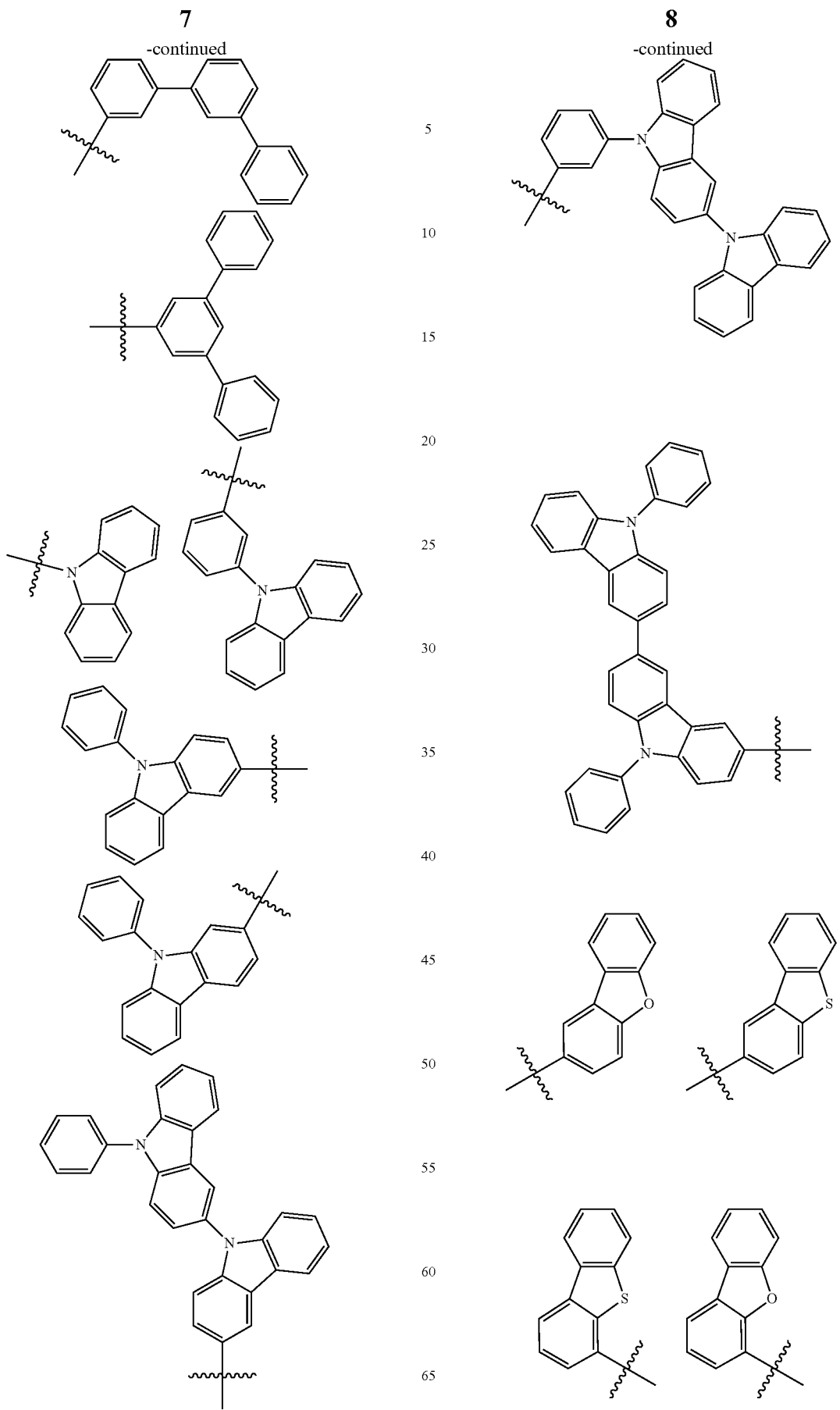

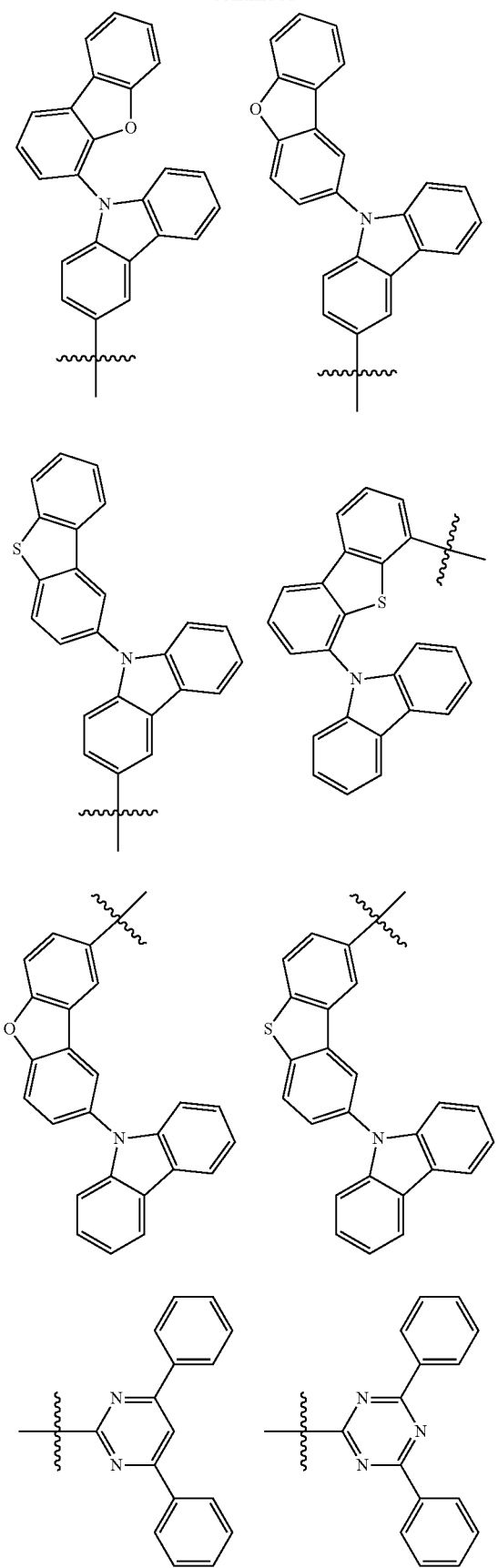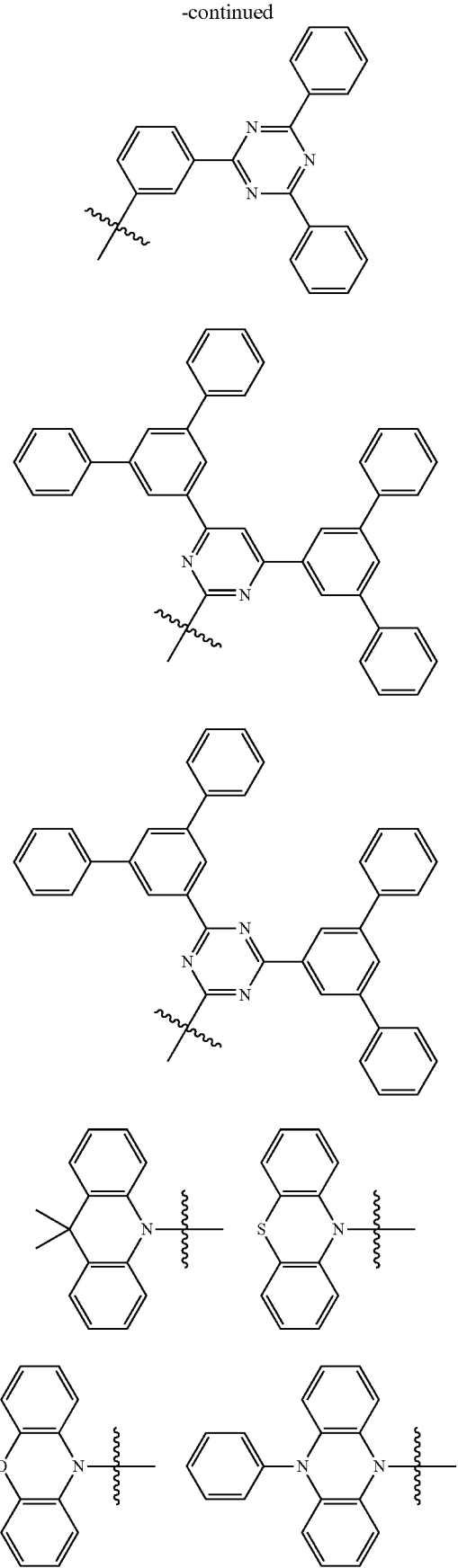

11
-continued
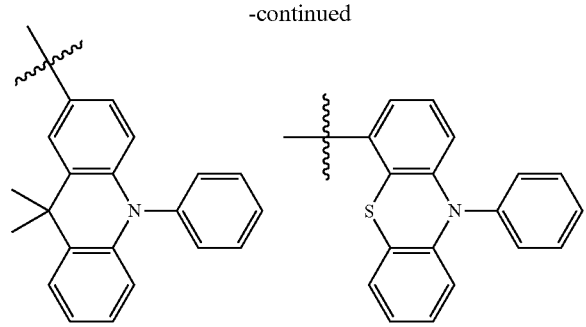
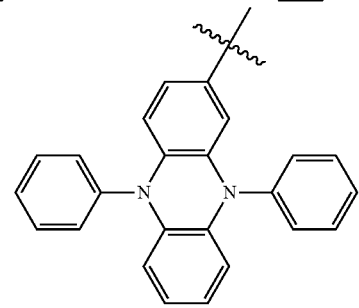
12
-continued
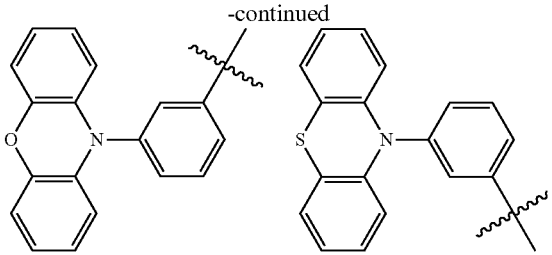
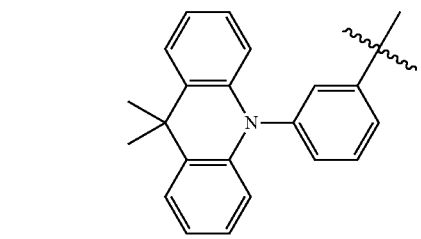
In this embodiment, some materials are shown below:
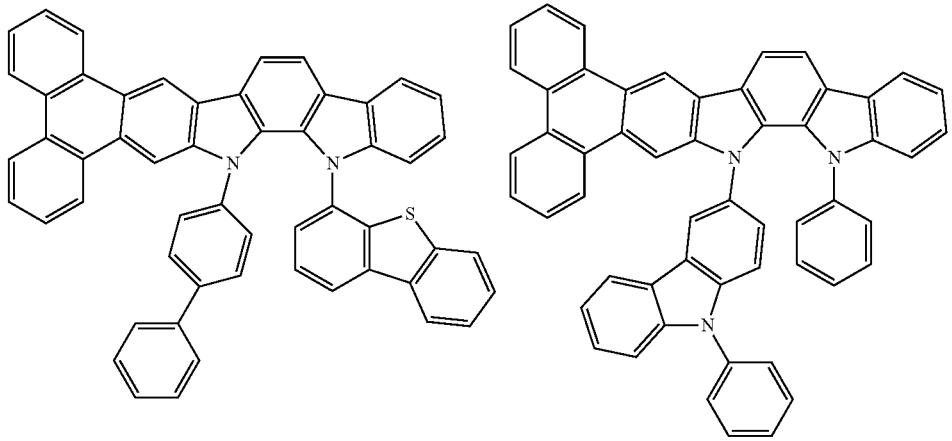
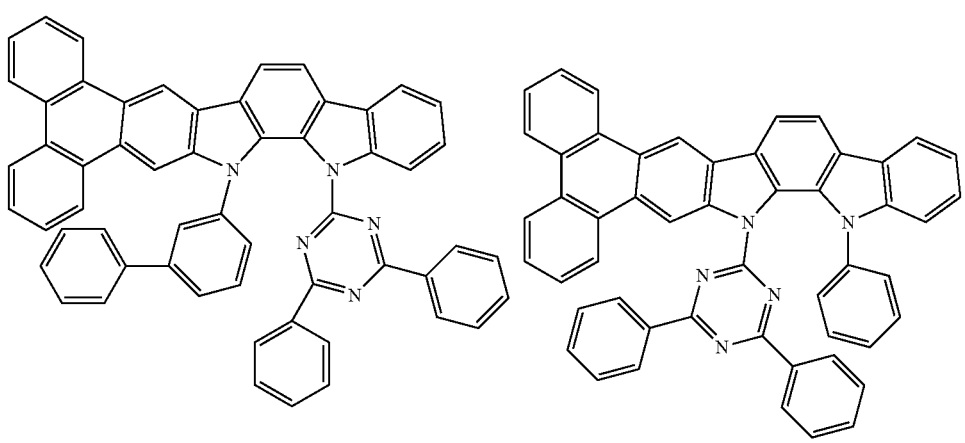

-continued
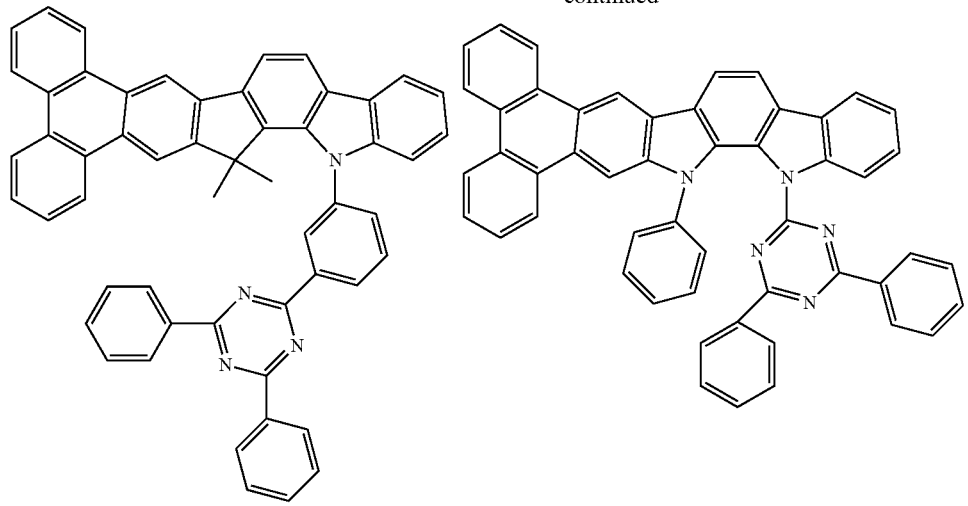
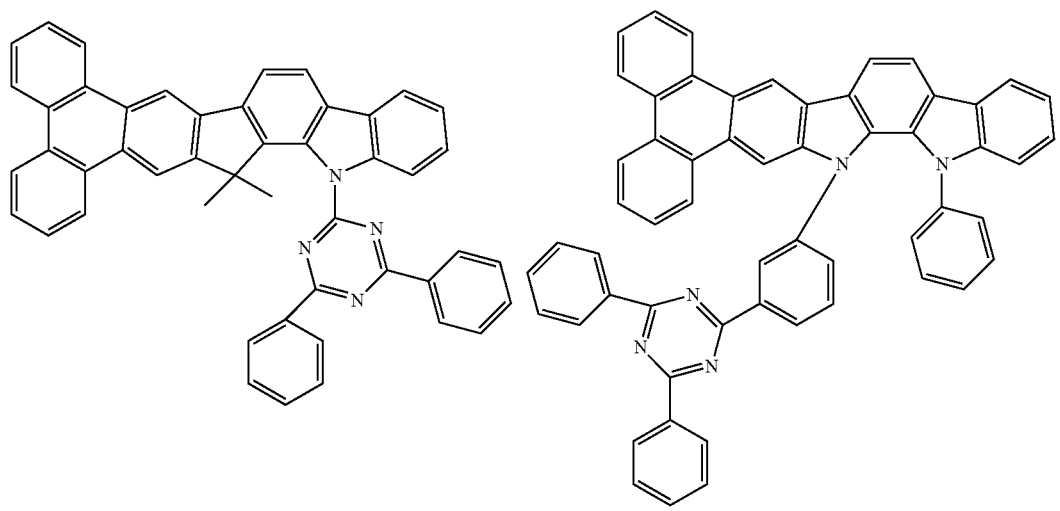
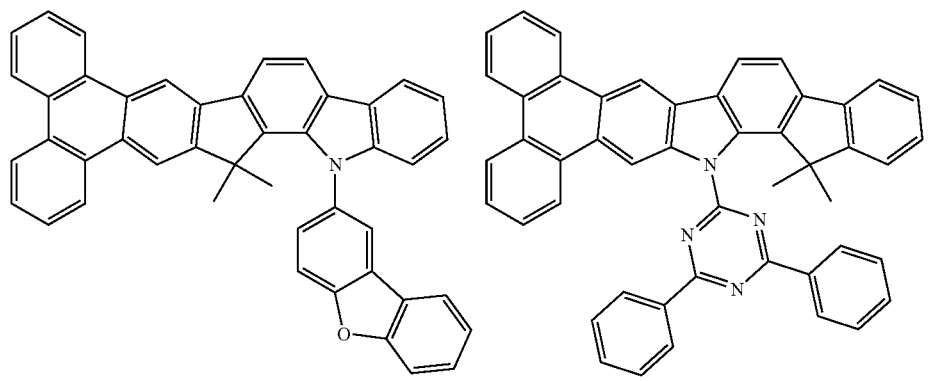

-continued
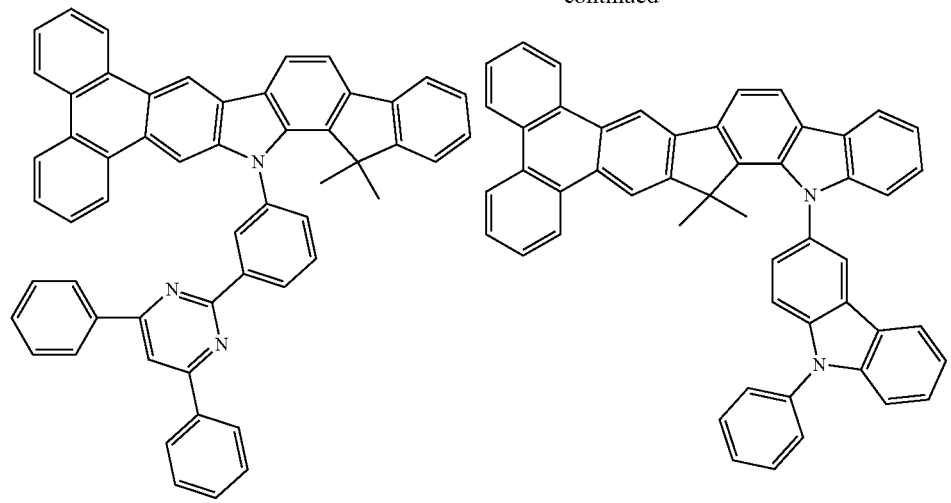
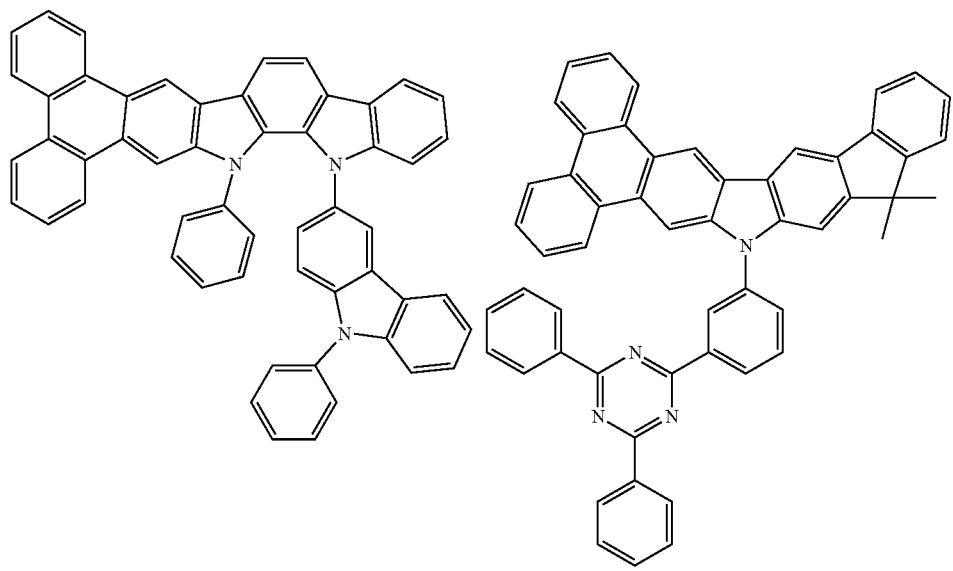
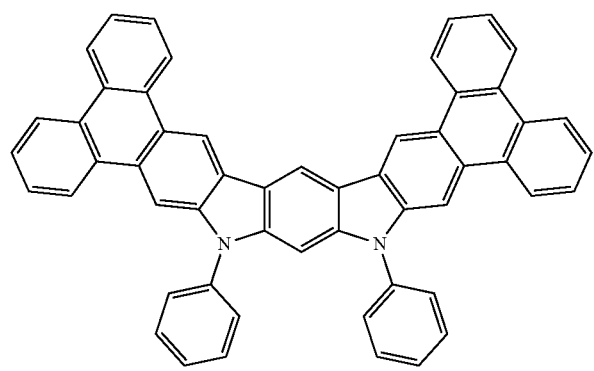

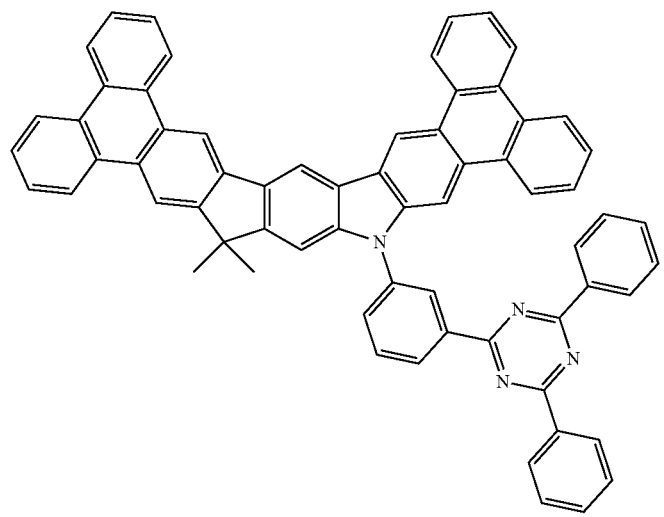
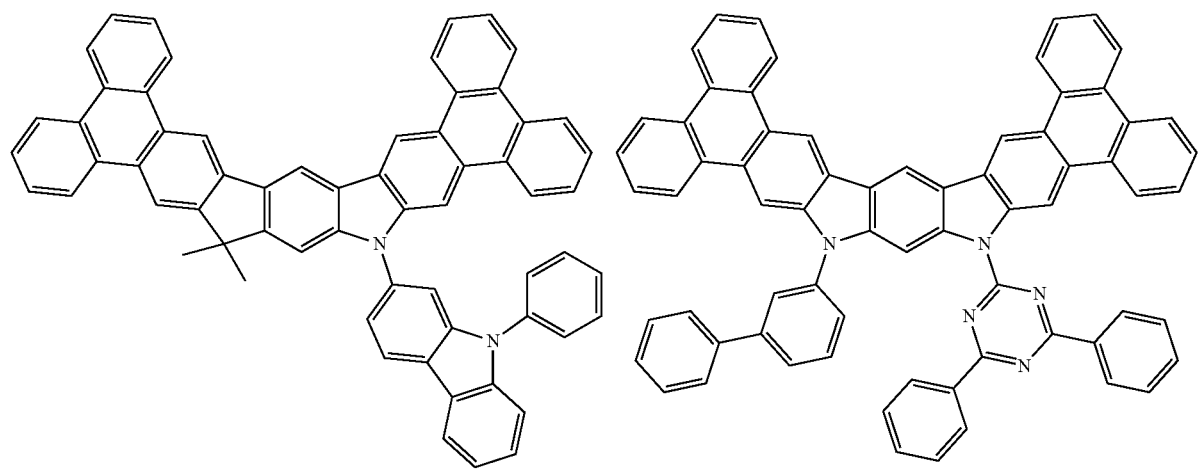
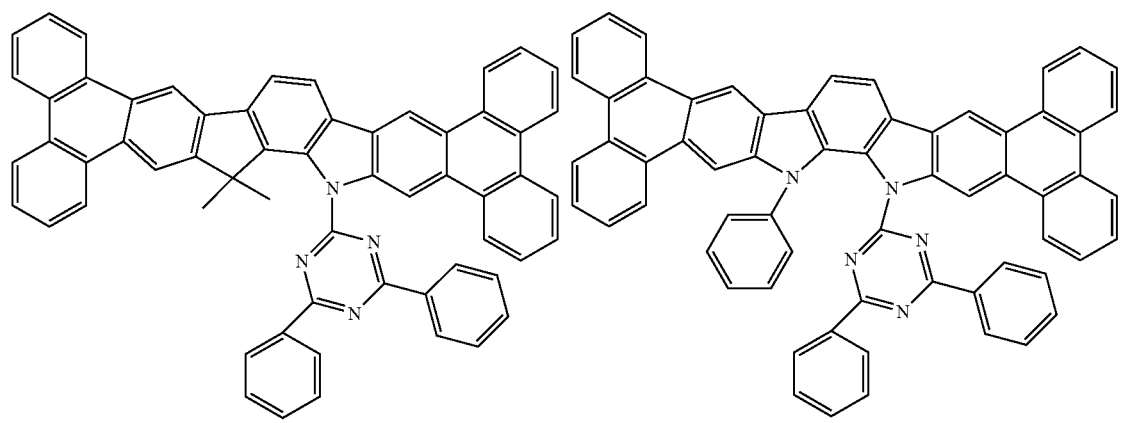

-continued
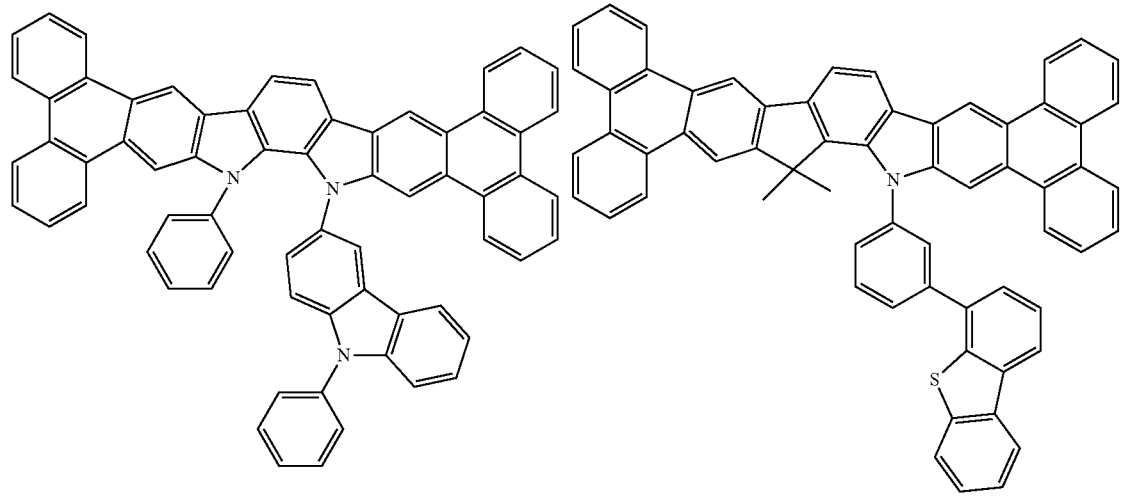
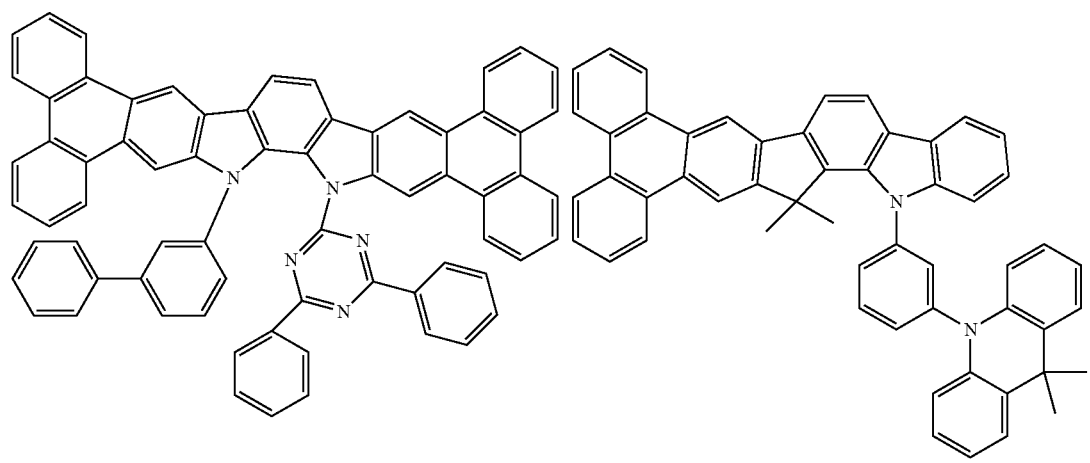
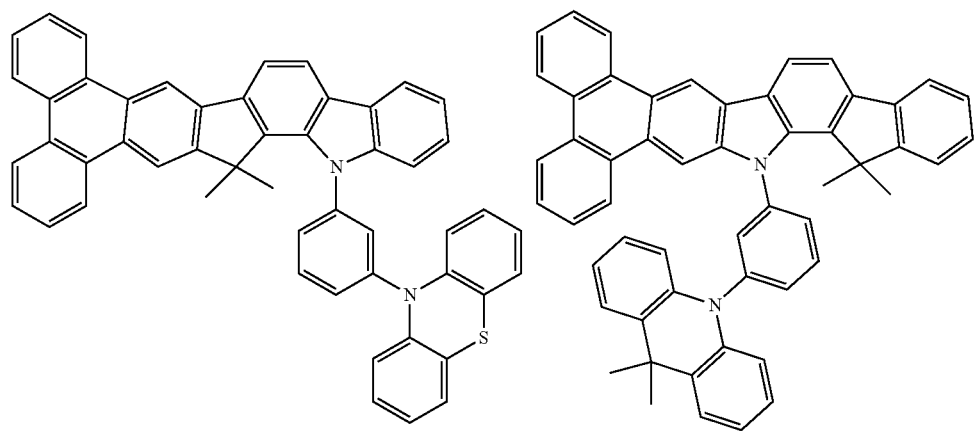

-continued
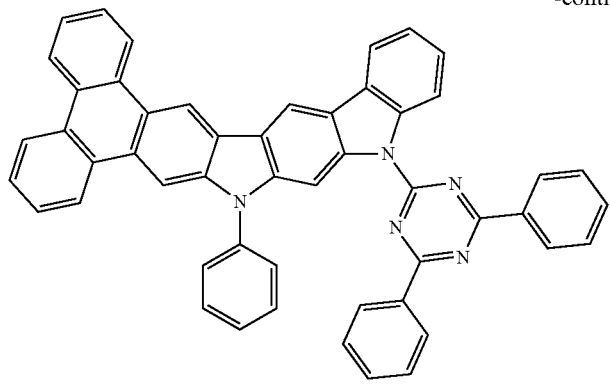
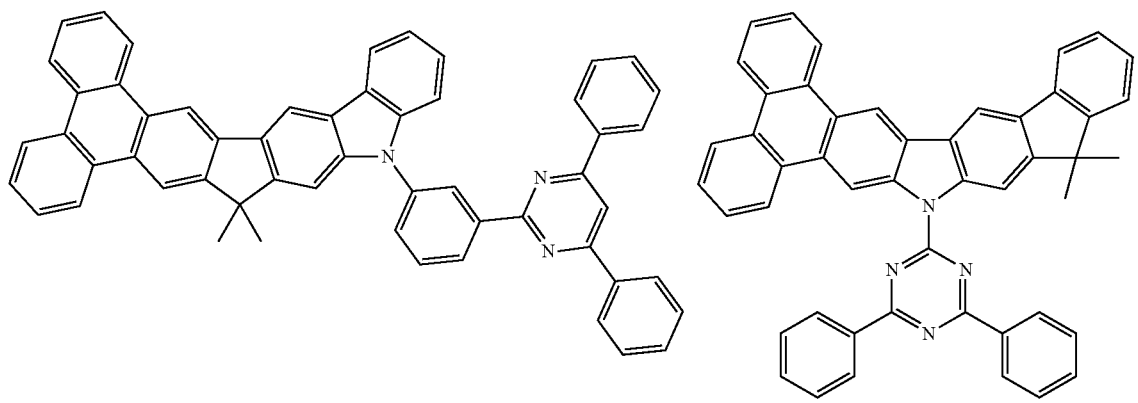
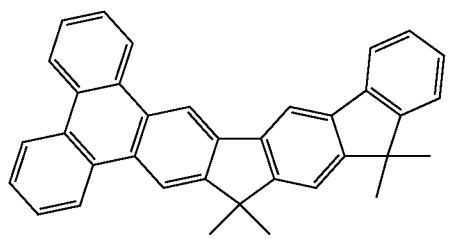
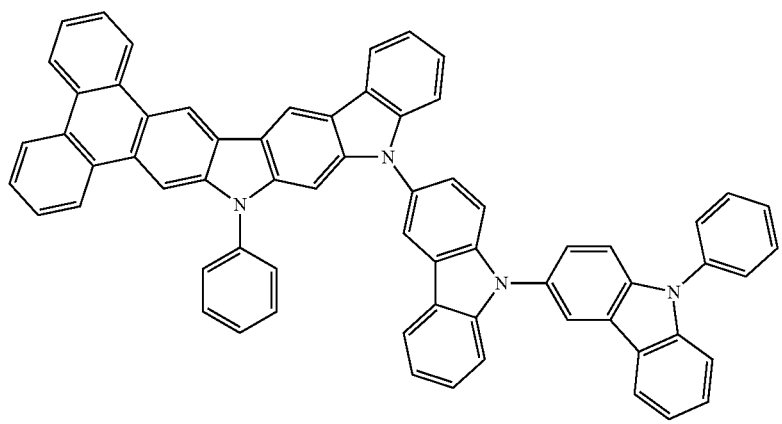

-continued
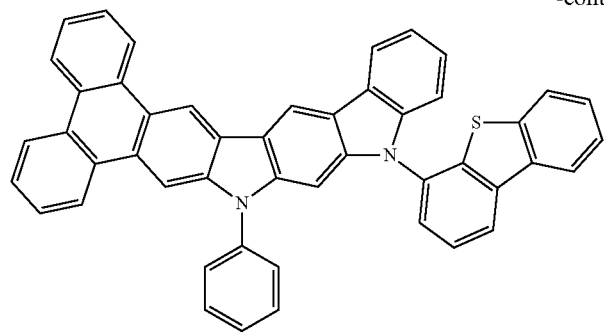
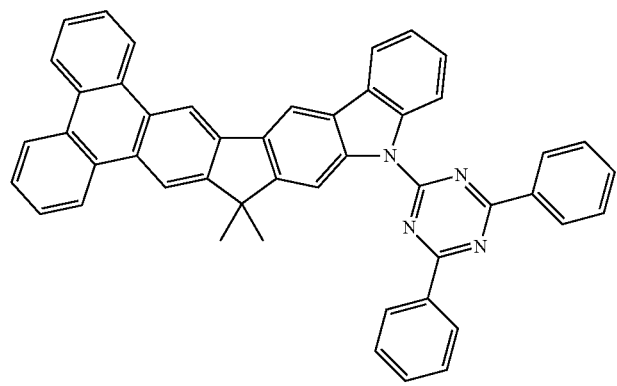
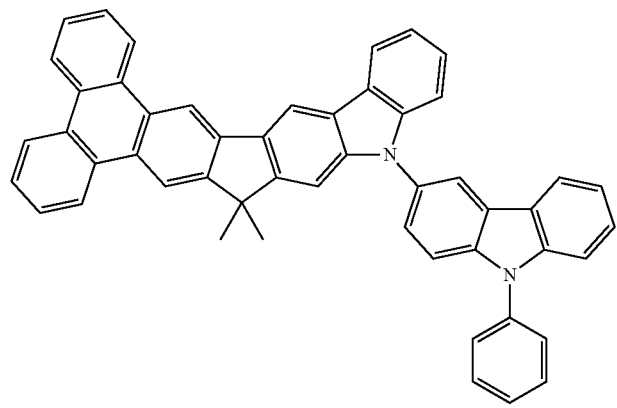
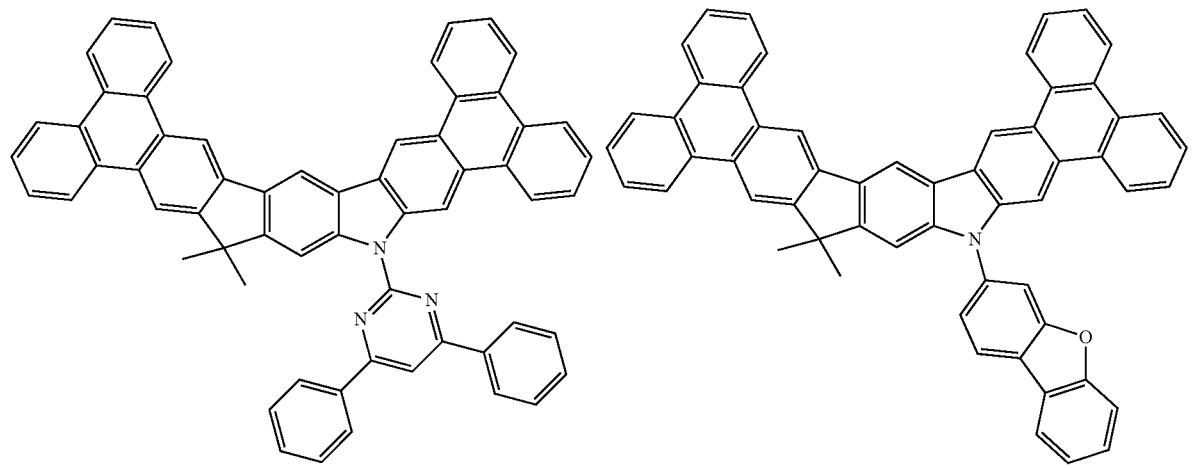

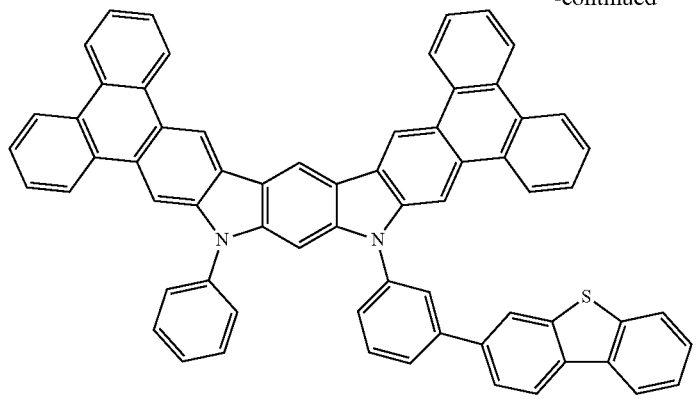

Detailed preparation for the compound in the present invention could be clarified by exemplary embodiments, but the present invention is not limited to exemplary embodiments. EXAMPLE 15 show the preparation for some EXAMPLES of the compound in the present invention. EXAMPLE 6~7 show the fabrication of organic EL device and I-V-B, half-life time of organic EL device testing report.

Example 1

Synthesis of 2-(biphenyl-2-yl)-7-bromo-9,9-dimethyl-9H-fluorene

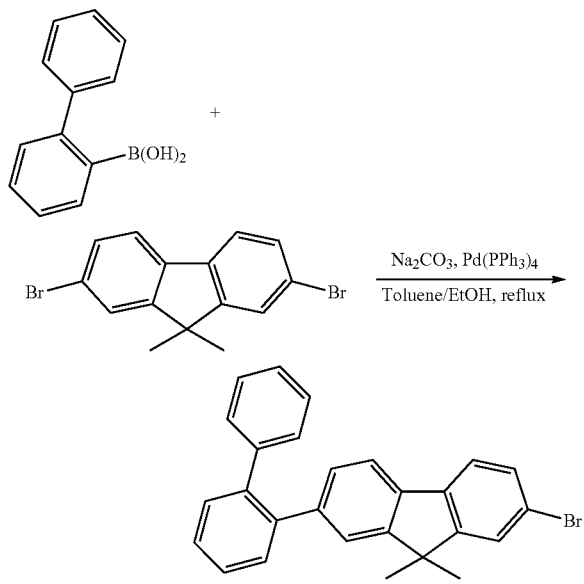

A mixture of 35.2 g (100 mmol) of 2,7-dibromo-9,9-dimethyl-9H-fluorene, 21.8 g (110 mmol) of biphenyl-2-ylboronic acid, 2.31 g (2 mmol) of Pd(PPh$_3$)$_4$, 75 ml of 2M Na$_2$CO$_3$, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (26.8 g, 63.0 mmol, 63%) as a white solid.

Synthesis of 12-bromo-10,10-dimethyl-10H-indeno[2,1-b]triphenylene

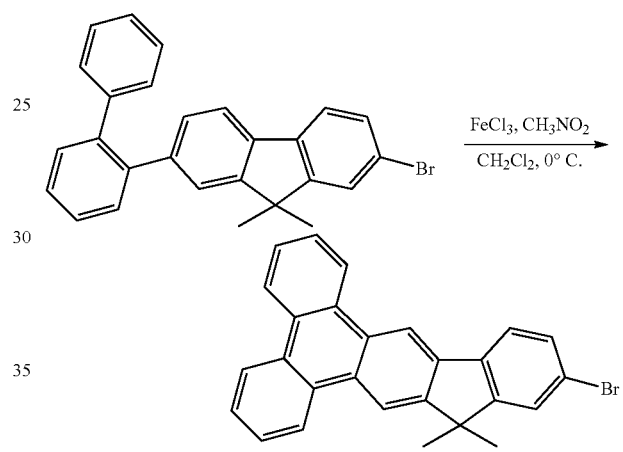

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous dichloromethane (1500 ml), 97.5 g (600 mmol) Iron (III)chloride was then added, and the mixture was stirred one hour. Methanol 500 ml were added to the mixture and the organic layer was separated and the solvent removed in vacuo. The residue was purified by column chromatography on silica(hexane-dichloromethane) afforded a white solid (10.7 g, 25.3 mmol, 40%). $^1$H NMR (CDCl3, 400 MHz): chemical shift (ppm) 8.95 (s, 1H), 8.79~8.74 (m, 2H), 8.69~8.68 (m, 3H), 7.84 (d, J=8.0 Hz, 1H), 7.72~7.65 (m, 5H), 7.57 (d, J=8.0 Hz, 1H), 1.66 (s, 6H).

Synthesis of 2-(10,10-dimethyl-10H-indeno[2,1-b]triphenylen-12-yl)-4,4,5,5-tetramethyl-1,3,2-dioxaborolane

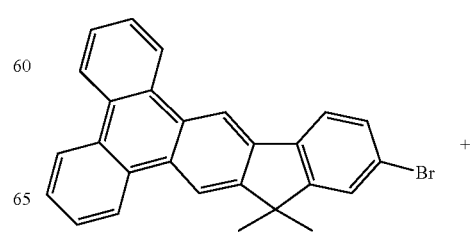

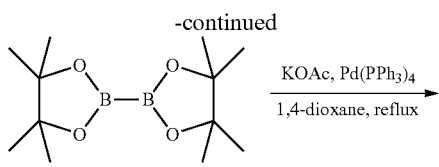

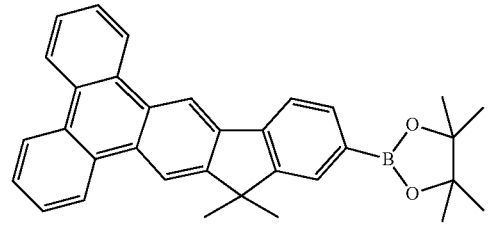

A mixture of 10.7 g (25.3 mmol) of 12-bromo-10,10-dimethyl-10H-indeno-[1,2-b]triphenylene, 7.7 g (30.3 mmol) of bis(pinacolato)diboron, 0.3 g (0.26 mmol) of Pd(PPh$_3$)$_4$, 7.4 g (75.4 mmol) of potassium acetate, and 300 ml 1,4-dioxane was degassed and placed under nitrogen, and then heated at 90° C. for 16 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (9.5 g, 20.2 mmol, 80%) as a light-yellow solid; $^1$H NMR (CDCl3, 400 MHz): chemical shift (ppm) 9.03 (s, 1H), 8.81 (d, J=7.84 Hz, 1H), 8.77 (d, J=7.88 Hz, 1H), 8.70~8.67 (m, 3H), 8.02~7.93 (m, 3H), 7.71~7.67 (m, 4H), 1.69 (s, 6H), 1.42 (s, 12H)

Synthesis of 10,10-dimethyl-12-(2-nitrophenyl)-10H-indeno[2,1-b]triphenylene

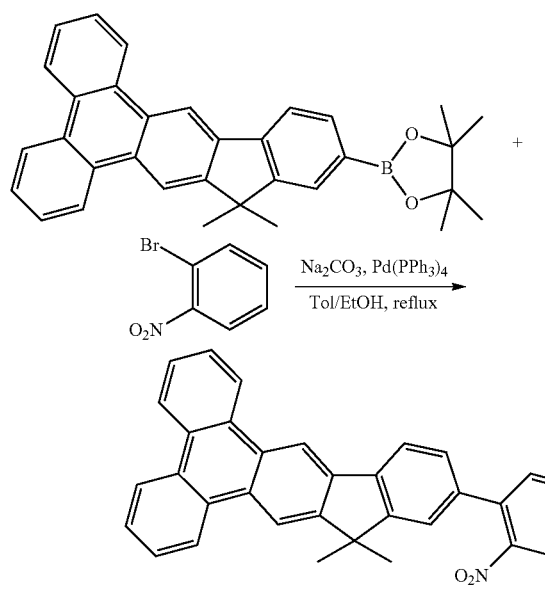

A mixture of 9.5 g (20.2 mmol) of 2-(10,10-dimethyl-10H-indeno[2,1-b]triphenylen-12-yl)-4,4,5,5-tetramethyl-1,3,2-dioxaborolane, 4.3 g (21 mmol) of 1-bromo-2-nitrobenzene, 0.44 g (0.4 mmol) of tetrakis(triphenyl phosphine)palladium, 30 ml of 2M Na$_2$CO$_3$, 40 ml of EtOH and 80 ml toluene was degassed and placed under nitrogen, and then heated at 90° C. overnight. After finishing the reaction, the mixture was allowed to cool to room temperature. The solution was extracted with 250 ml of ethyl acetate and 1000 ml of water. The organic layer was dried with anhydrous magnesium sulfate and the solvent was evaporated under reduced pressure. The residue was purified by column chromatography on silica (Hx-EA) to give product 5.5 g (58%).

Synthesis of Intermediate I

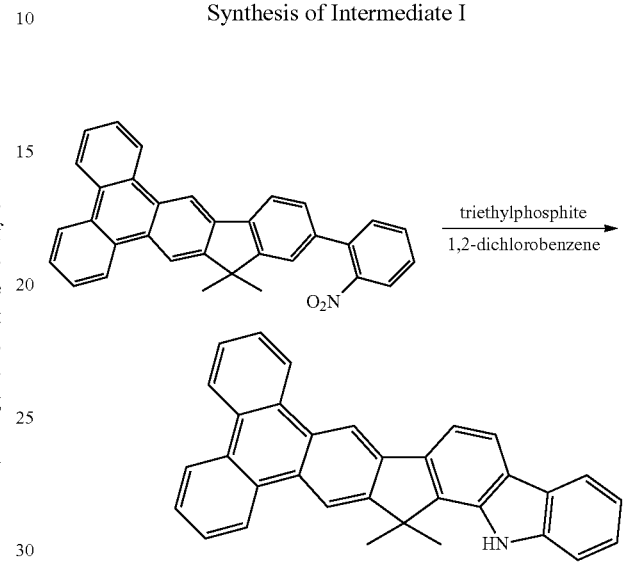

A mixture of 5.5 g (11.8 mmol) of 10,10-dimethyl-12-(2-nitro phenyl)-10H-indeno[2,1-b]triphenylene, 30 ml of triethylphosphite, 15 ml of 1,2-dichlorobenzene, was placed under nitrogen, and then heated at 160° C. overnight. After finishing the reaction, the mixture was allowed to cool to room temperature. Than 200 ml of MeOH was added, while stirring and the precipitated product was filtered off with suction. To give 1.9 g (yield 37%) of yellow product which was purified by column chromatography on silica (Hx-CH$_2$Cl$_2$).

Synthesis of Example 1

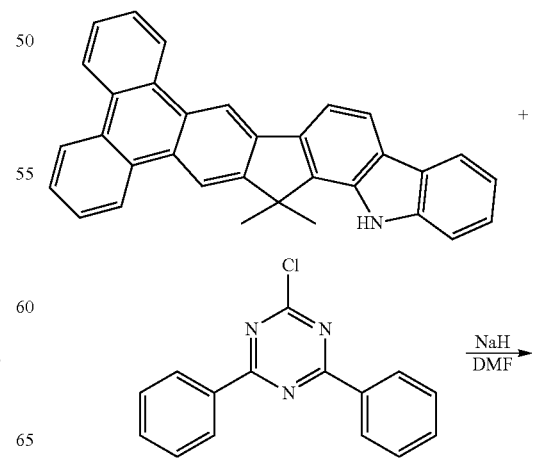

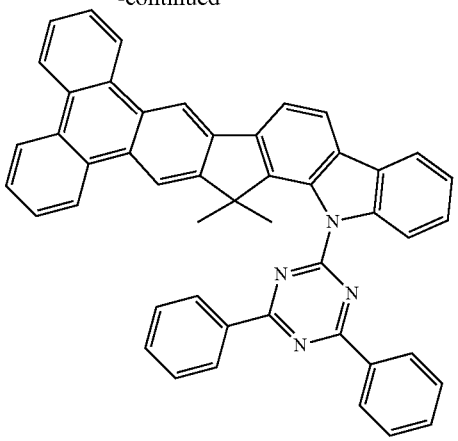

Under N$_2$ condition, 1.9 g (4.4 mmol) of intermediate I and 50 ml of DMF were mixed, and 0.85 g (35.2 mmol) of NaH was slowly added to the mixture. The mixture was stirred at room temperature for 30 minutes. Than 3.5 g (13.2 mmol) of 2-chloro-4,6-diphenyl-1,3,5-triazine was slowly added to the mixture. The mixture was stirred at room temperature for 24 hours. After completion of the reaction, 200 ml of iced water was added, while stirring and the precipitated product was filtered off with suction. To give 1.4 g (yield 48%) of yellow product which was recrystallized from ethyl acetate. MS (m/z, FAB$^+$): 664.5; $^1$H NMR (CDCl$_3$, 400 MHz): chemical shift (ppm) 9.02 (s, 1H), 8.83~8.75 (m, 5H), 8.54~8.48 (m, 4H), 8.42~8.23 (m, 2H), 8.07~7.98 (m, 6H), 7.87~7.81 (m, 2H), 7.76~7.51 (m, 5H), 7.38~7.28 (d, J=8.0 Hz, 1H), 1.83 (s, 6H).

Example 2

Synthesis of Intermediate II

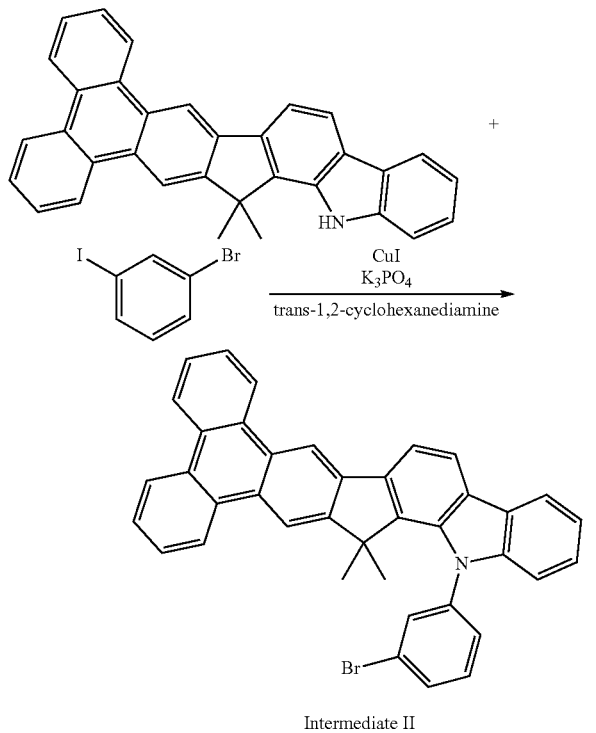

Intermediate II

A mixture of 15.7 g (36.2 mmole) intermediate I, 10.2 g (36.2 mmole) of 1-bromo-3-iodobenzene, 17.1 g (90 mmole) of copper(I) iodide, 19.1 g (90 mmole) of potassium phosphate, 10.3 g (90 mmole) of trans-1,2-cyclohexane diamine and 1,4-dioxane 700 ml were refluxed under nitrogen for about overnight. Then, the solution was filtered at 110° C. To receive the filtrate, And the 1,4-dioxane was removed under reduced pressure from the filtrate. The filtrate was extracted with 500 ml dichloromethane and 2000 ml water, the organic layer was dried with anhydrous magnesium sulfate, the solvent was removed and the residue was purified by column chromatography on silica (hexane-ethyl acetate) to give product 12.1 g (57%).

Synthesis of Intermediate III

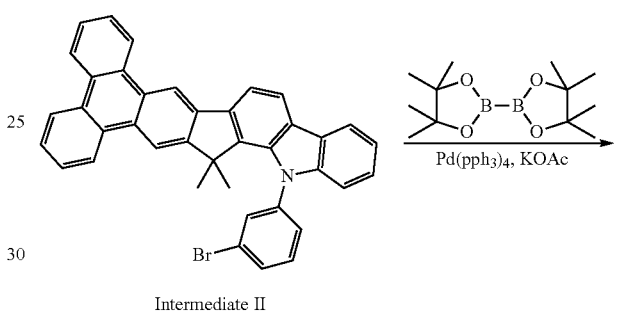

Intermediate II

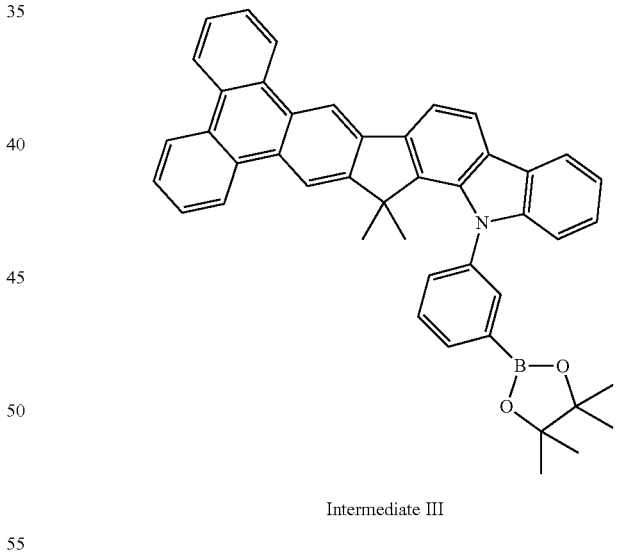

Intermediate III

A mixture of 12.1 g (20.6 mmol) of intermediate II, 7.8 g (31 mmol) of bis(pinacolato)diboron, 0.48 (0.4 mmol) of tetrakis(triphenylphosphine) palladium, 4.1 g (41.2 mmol) of potassium acetate, and 200 ml of 1,4-dioxane was degassed and placed under nitrogen, and then heated at 90° C. for 24 h. After finishing the reaction, the mixture was allowed to cool to room temperature. The organic layer was extracted with ethyl acetate and water, dried with anhydrous magnesium sulfate, the solvent was removed and the product was purified by column using a mixture of hexanes and ethyl acetate as eluent to get 8.2 g of light yellow product (yield 63%).

Synthesis of Example 2

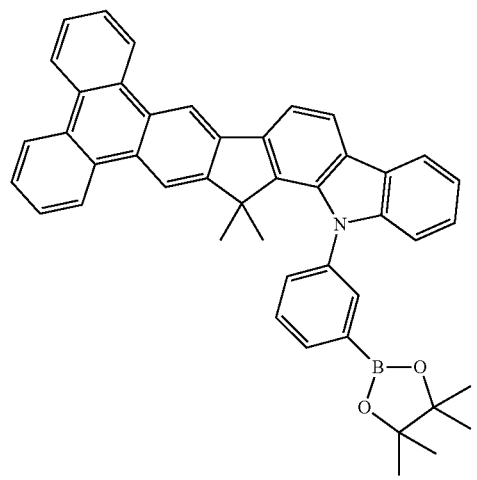

Intermediate III

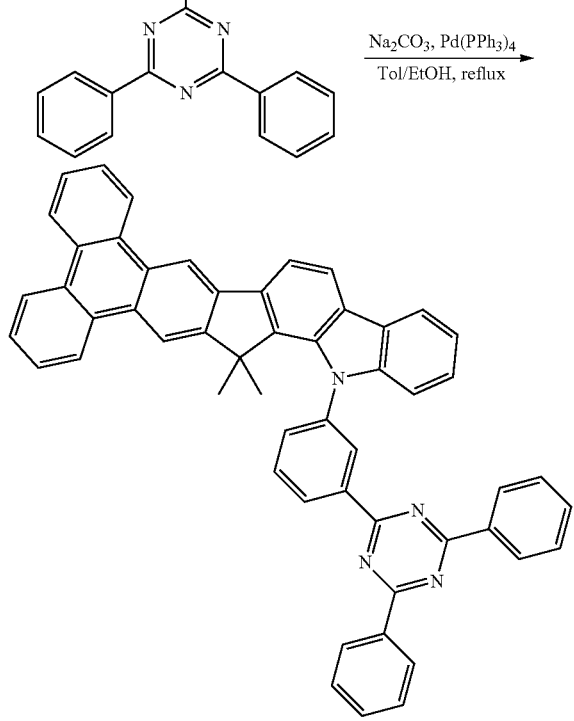

A mixture of 6.4 g (10.1 mmol) of intermediate III, 5.4 g (20 mmol) of 2-chloro-4,6-diphenyl-1,3,5-triazine, 0.22 g (0.2 mmol) of tetrakis(triphenyl phosphine)palladium, 15 ml of 2M Na$_2$CO$_3$, 20 ml of EtOH and 40 ml toluene was degassed and placed under nitrogen, and then heated at 90° C. overnight. After finishing the reaction, the mixture was allowed to cool to room temperature. Than 100 ml of MeOH was added, while stirring and the precipitated product was filtered off with suction. To give 4 g (yield 53%) of yellow product which was recrystallized from toluene. MS (m/z, FAB$^+$): 740.4 $^1$H NMR (CDCl$_3$, 400 MHz): chemical shift (ppm) 9.02 (s, 1H), 8.81~8.72 (m, 6H), 8.52~8.43 (m, 8H), 8.42~8.23 (m, 2H), 8.07~7.98 (m, 6H), 7.87~7.83 (m, 2H), 7.66~7.51 (m, 5H), 1.79 (s, 6H).

Example 3

Synthesis of 3-(biphenyl-2-yl)-6-bromo-9-phenyl-9H-carbazole

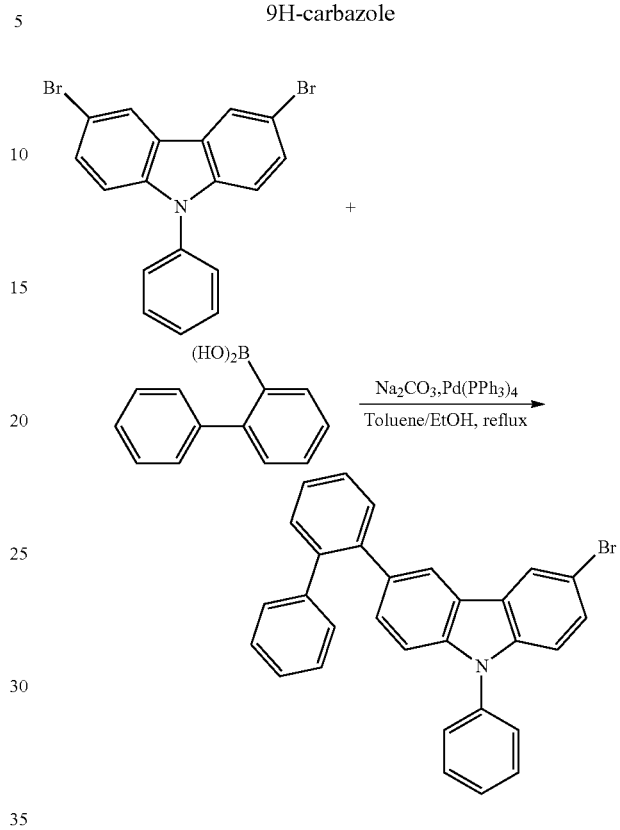

A mixture of 40.1 g (100 mmol) of 3,6-dibromo-9-phenyl-9H-carbazole, 21.8 g (110 mmol) of biphenyl-2-ylboronic acid, 2.31 g (2 mmol) of Pd(PPh$_3$)$_4$, 75 ml of 2M Na$_2$CO$_3$, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (19.9 g, 42.0 mmol, 42%) as a white solid.

Synthesis of 13-bromo-10-phenyl-10H-phenanthro[9,10-b]carbazole

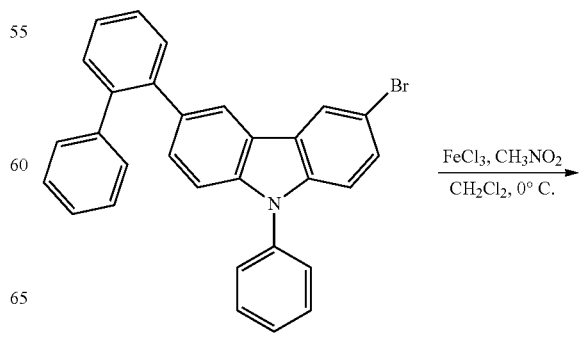

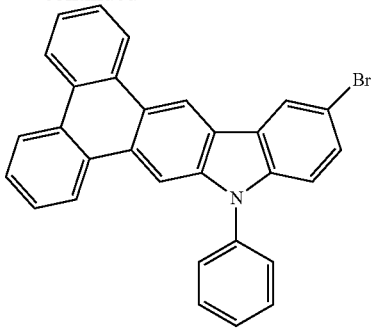

In a 3000 ml three-necked flask that had been degassed and filled with nitrogen, 19.9 g (42 mmol) of 3-(biphenyl-2-yl)-6-bromo-9-phenyl-9H-carbazole was dissolved in anhydrous dichloromethane (1000 ml), 68.2 g (420 mmol) Iron(III) chloride was then added, and the mixture was stirred 10 minutes. Methanol 300 ml were added to the mixture and the organic layer was separated and the solvent removed in vacuo. The residue was purified by column chromatography on silica(hexane-dichloromethane) afforded a white solid (14.5 g, 30.7 mmol, 73%).

Synthesis of 10-phenyl-13-(4,4,5,5-tetramethyl-1,3,2-dioxaborolan-2-yl)-10H-phenanthro[9,10-b]carbazole

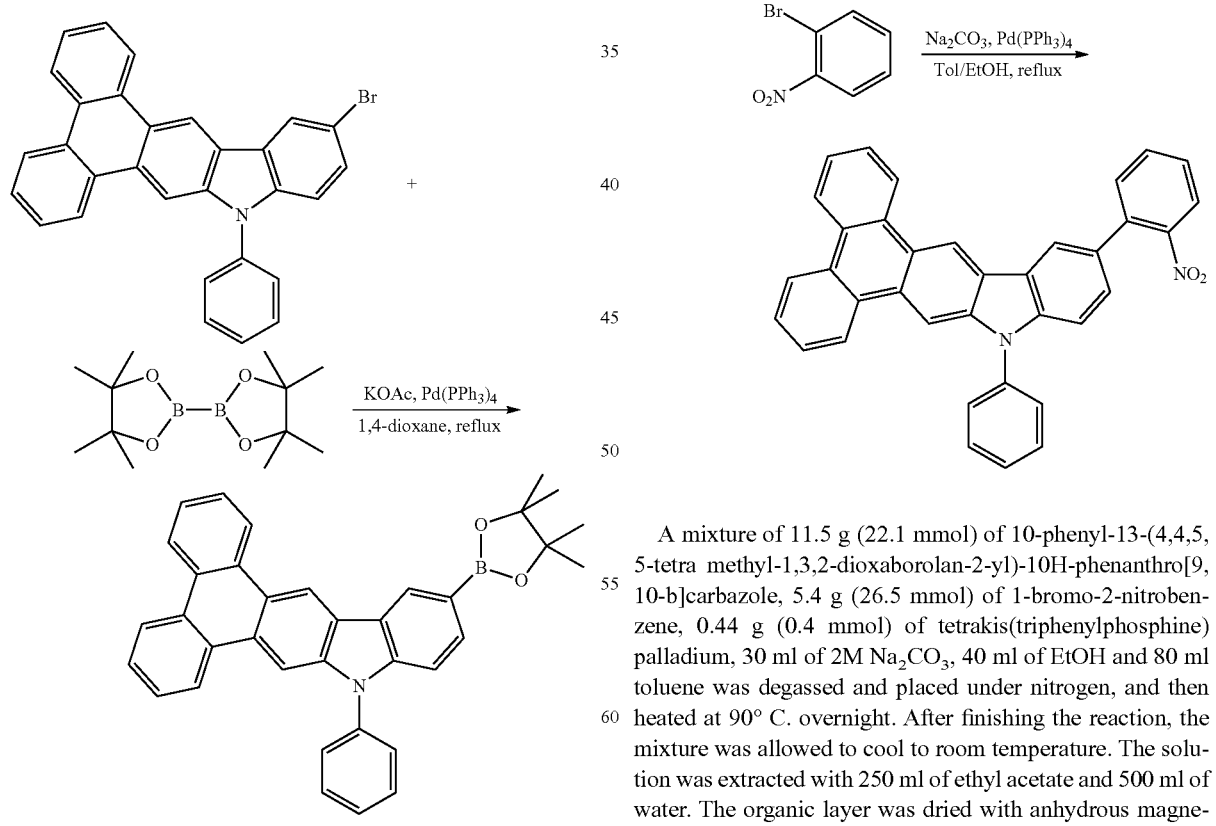

A mixture of 14.5 g (30.7 mmol) of 13-bromo-10-phenyl-10H-phenanthro[9,10-b]carbazole, 11.8 g (46 mmol) of bis(pinacolato)diboron, 0.46 g (0.4 mmol) of Pd(PPh$_3$)$_4$, 11.3 g (115.4 mmol) of potassium acetate, and 300 ml 1,4-dioxane was degassed and placed under nitrogen, and then heated at 120° C. for 16 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-ethyl acetate) to give product (11.5 g, 22.1 mmol, 72%) as a light-yellow solid.

Synthesis of 13-(2-nitrophenyl)-10-phenyl-10H-phenanthro[9,10-b]carbazole

A mixture of 11.5 g (22.1 mmol) of 10-phenyl-13-(4,4,5,5-tetra methyl-1,3,2-dioxaborolan-2-yl)-10H-phenanthro[9,10-b]carbazole, 5.4 g (26.5 mmol) of 1-bromo-2-nitrobenzene, 0.44 g (0.4 mmol) of tetrakis(triphenylphosphine) palladium, 30 ml of 2M Na$_2$CO$_3$, 40 ml of EtOH and 80 ml toluene was degassed and placed under nitrogen, and then heated at 90° C. overnight. After finishing the reaction, the mixture was allowed to cool to room temperature. The solution was extracted with 250 ml of ethyl acetate and 500 ml of water. The organic layer was dried with anhydrous magnesium sulfate and the solvent was evaporated under reduced pressure. The residue was purified by column chromatography on silica (Hx-EA) to give product 7.8 g (69%).

Synthesis of Intermediate A

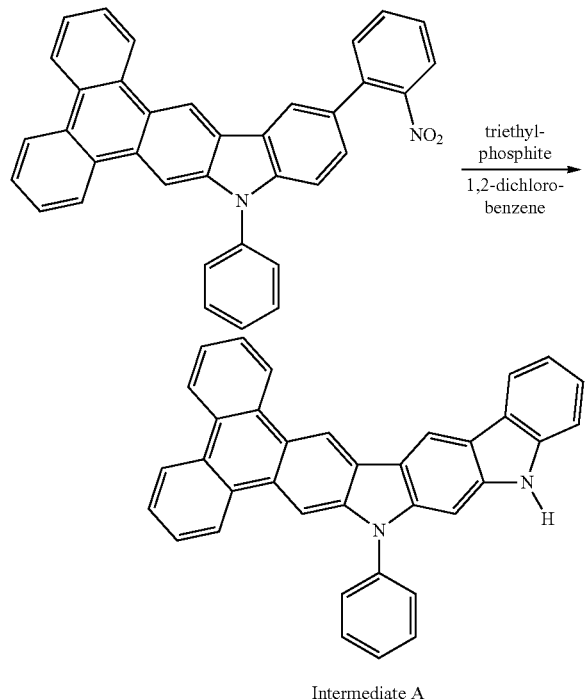

Intermediate A

A mixture of 7.8 g (15.2 mmol) of 12-(2-nitrophenyl)-10-phenyl-10H-phenanthro[9,10-b]carbazole, 50 ml of triethylphosphite, 20 ml of 1,2-dichlorobenzene, was placed under nitrogen, and then heated at 160° C. overnight. After finishing the reaction, the mixture was allowed to cool to room temperature. Than 200 ml of MeOH was added, while stirring and the precipitated product was filtered off with suction. To give 4.3 g (yield 59%) of yellow product which was purified by column chromatography on silica (Hx-CH$_2$Cl$_2$).

Synthesis of Example 3

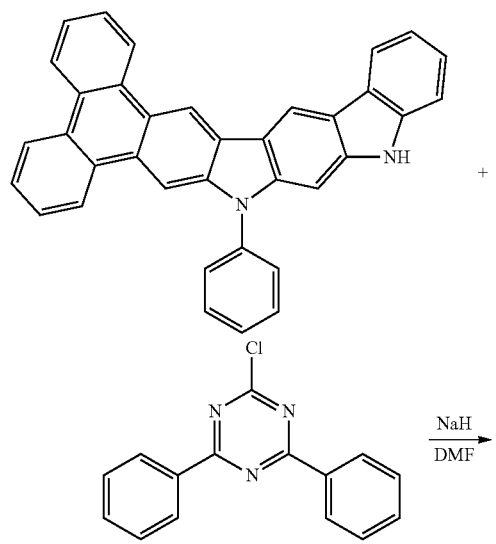

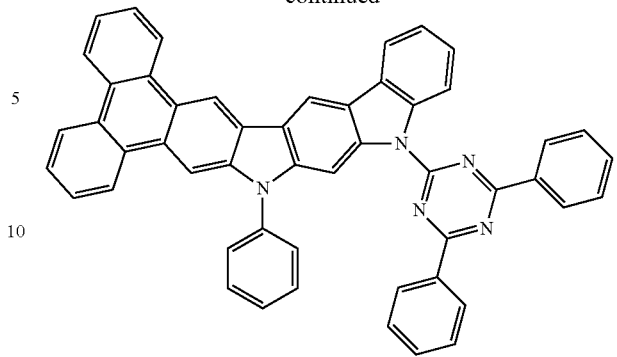

Under N$_2$ condition, 4.3 g (8.9 mmol) of intermediate A and 50 ml of DMF were mixed, and 0.86 g (35.6 mmol) of NaH was slowly added to the mixture. The mixture was stirred at room temperature for 30 minutes. Than 3.5 g (13.2 mmol) of 2-chloro-4,6-diphenyl-1,3,5-triazine was slowly added to the mixture. The mixture was stirred at room temperature for 24 hours. After completion of the reaction, 200 ml of iced water was added, while stirring and the precipitated product was filtered off with suction. To give 2.7 g (yield 43%) of yellow product which was recrystallized from ethyl acetate. MS (m/z, FAB$^+$): 713.6; $^1$H NMR (CDCl$_3$, 400 MHz): chemical shift (ppm) 9.12 (s, 1H), 8.89~8.83 (m, 2H), 8.76 (d, J=8.00 Hz, 2H), 8.61~8.56 (m, 4H), 8.45 (d, J=9.20 Hz, 2H), 8.03~7.92 (m, 6H), 7.89~7.83 (m, 2H), 7.78~7.64 (m, 6H), 7.50~7.44 (m, 4H), 7.36~7.29 (m, 2H)

Example 4

Synthesis of 3,8-dibromo-11,12-dihydroindolo[2,3-a]carbazole

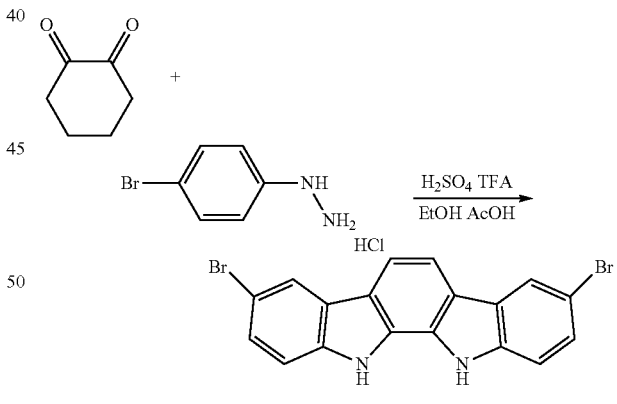

In a 1000 ml three-necked flask that had been degassed and filled with nitrogen, 44.7 g (200 mmole) 4-Bromophenylhydrazine hydrochloride, 11.2 g (100 mmole) of cyclohexane-1,2-dione, were dissolved in 500 ml EtOH, 5 ml of H$_2$SO$_4$ was added dropwise to the solution at room temperature, and then heated at 80° C. for 4 h. After finishing the reaction, the mixture was allowed to cool to room temperature. The resulting solid was filtered off, washed with ethanol to give 38 g of red powder. The 38 g of red powder was dissolved in 380 ml of glacial acetic acid, 38 g of trifluoroacetic acid was then added, and then heated at 100° C. for 24 h. After finishing the reaction, the mixture was allowed to cool to room temperature. The resulting solid was filtered off, washed with hexane and ethanol to give product 15.3 g (37%).

Synthesis of 3,8-di(biphenyl-2-yl)-11,12-dihydroindolo[2,3-a]carbazole

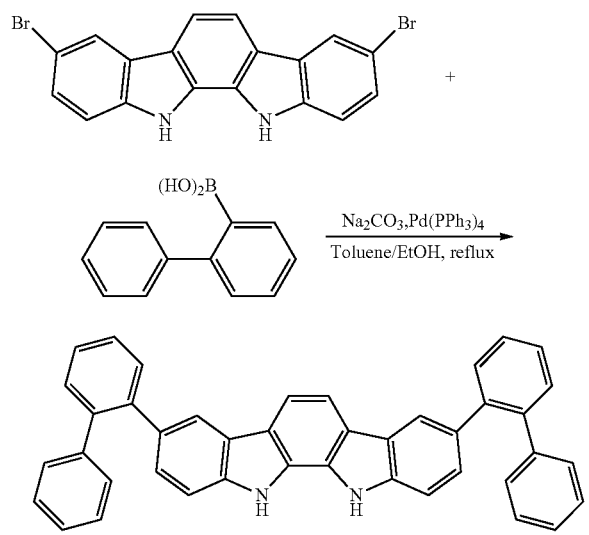

A mixture of 15.3 g (37 mmol) of 3,8-dibromo-11,12-dihydroindolo[2,3-a]carbazole, 18.3 g (92.4 mmol) of biphenyl-2-ylboronic acid, 0.86 g (0.8 mmol) of Pd(PPh$_3$)$_4$, 55 ml of 2M Na$_2$CO$_3$, 100 ml of EtOH and 200 ml toluene was degassed and placed under nitrogen, and then heated at 100° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (12.2 g, 21.8 mmol, 59%).

Synthesis of Intermediate B

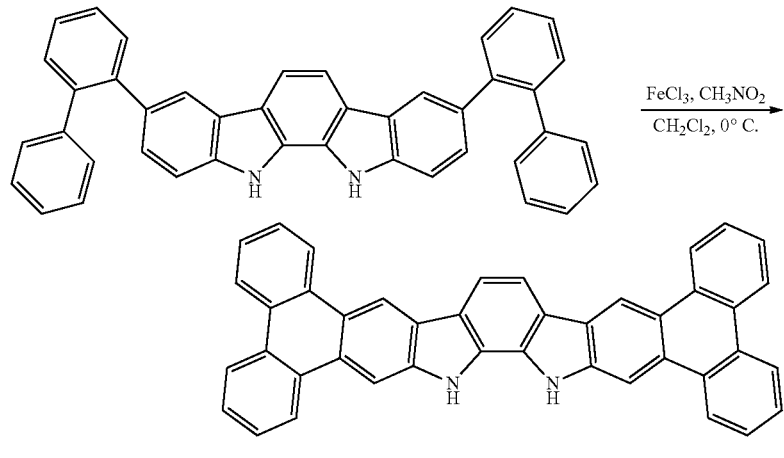

Intermediate B

In a 2000 ml three-necked flask that had been degassed and filled with nitrogen, 12.2 g (21.8 mmol) of 3,8-di(biphenyl-2-yl)-11,12-dihydroindolo[2,3-a]carbazole was dissolved in anhydrous dichloromethane (500 ml), 34.1 g (210 mmol) Iron(III) chloride was then added, and the mixture was stirred 10 minutes. Methanol 100 ml were added to the mixture and the organic layer was separated and the solvent removed in vacuo. The residue was purified by column chromatography on silica (hexane-dichloromethane) afforded a yellow solid (4.3 g, 36%).

Synthesis of Intermediate C

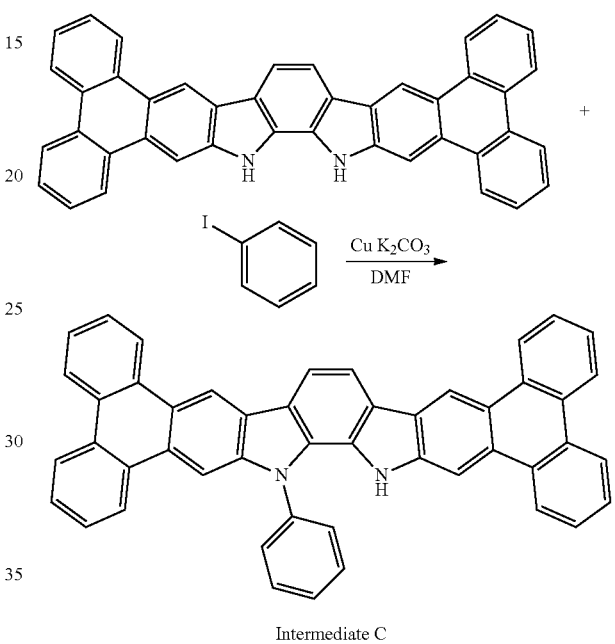

Intermediate C

Under nitrogen, 4.3 g (7.7 mmol) of intermediate B was added to a flask together with 1.73 g (8.5 mmol) of iodobenzene, potassium carbonate (8.5 g, 62 mmol), copper (3.9 g, 62 mmol) and 50 ml of DMF. The reaction was heated to 160° C. for 48 h. The mixture was cooled to room temperature and diluted with 300 ml of CH$_2$Cl$_2$, 300 ml of water are added to the mixture. The organic phase was dried over sodium sulfate and concentrated. The resulting crude product was purified by chromatography to obtained 1.8 g of product. Yield 37%.

Synthesis of Example 4

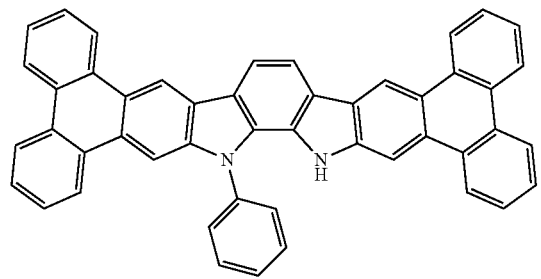

Intermediate C

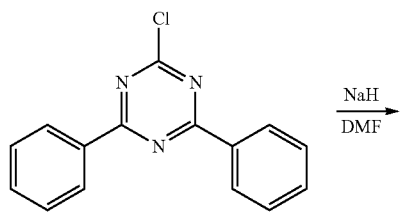

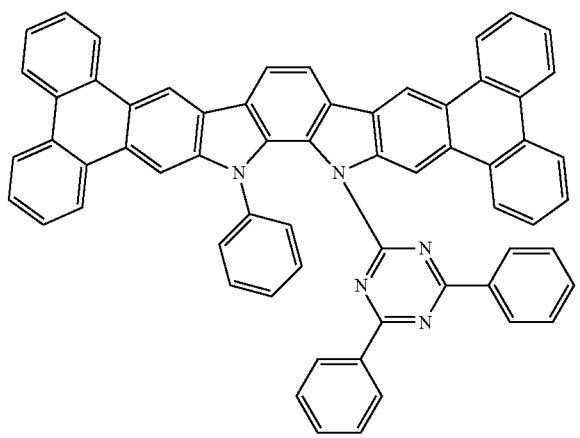

Under N$_2$ condition, 1.8 g (2.9 mmol) of intermediate C and 30 ml of DMF were mixed, and 0.56 g (23.2 mmol) of NaH was slowly added to the mixture. The mixture was stirred at room temperature for 30 minutes. Than 2.4 g (8.7 mmol) of 2-chloro-4,6-diphenyl-1,3,5-triazine was slowly added to the mixture. The mixture was stirred at room temperature for 24 hours. After completion of the reaction, 200 ml of iced water was added, while stirring and the precipitated product was filtered off with suction. To give 1.3 g (yield 51%) of yellow product which was recrystallized from ethyl acetate. MS (m/z, FAB$^+$): 864.2; $^1$H NMR (CDCl$_3$, 400 MHz): chemical shift (ppm) 9.09 (s, 2H), 8.97~8.93 (m, 4H), 8.57~8.41 (m, 7H), 8.23 (d, J=8.0 Hz, 2H), 8.13~7.92 (m, 8H), 7.89~7.83 (m, 2H), 7.78~7.64 (m, 6H), 7.45~7.39 (m, 4H), 7.36~7.29 (m, 2H)

Example 5

Synthesis of Example 5

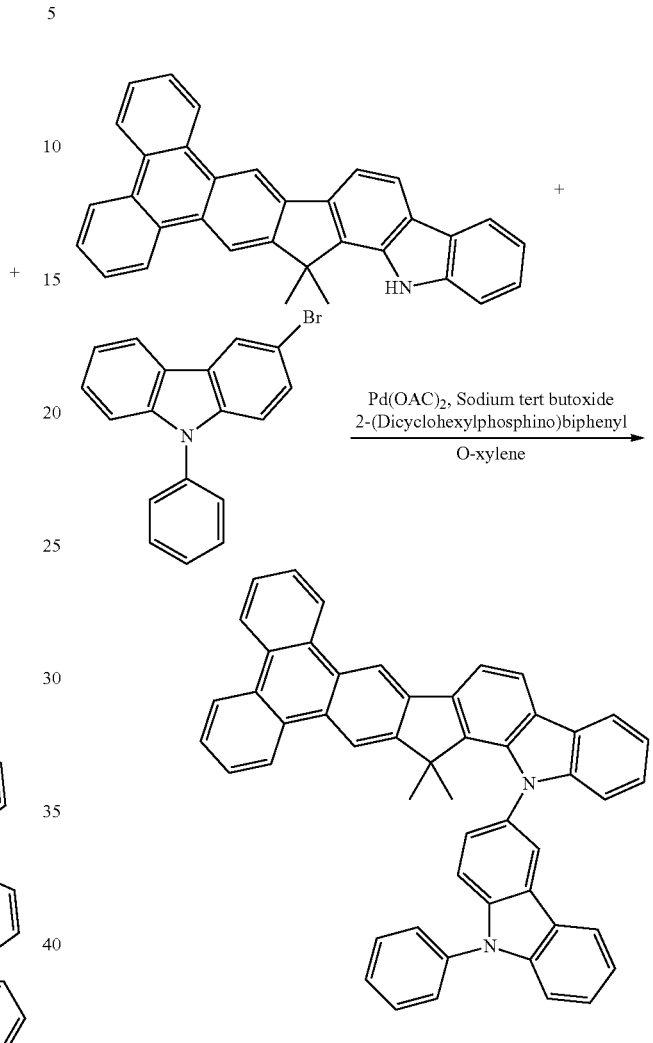

A mixture of 4.3 g (10 mmol) intermediate I, 4.8 g (15 mmol) of 3-bromo-9-phenyl-9H-carbazole, 0.05 g (0.2 mmol) of palladium(II)acetate, 0.15 g (0.4 mmol) of 2-(dicyclohexylphosphino)biphenyl, 2 g (20 mmol) of sodium tert-butoxide and 100 ml of o-xylene was refluxed under nitrogen overnight. After finishing the reaction, the solution was filtered at 100° C., To receive the filtrate, and the filtrate was added to 1 L MeOH, while stirring and the precipitated product was filtered off with suction. To give 3.2 g (yield 48%) of yellow product which was recrystallized from toluene. MS (m/z, FAB$^+$): 674.5; $^1$H NMR (CDCl$_3$, 400 MHz): chemical shift (ppm) 9.11 (s, 1H), 8.76~8.71 (m, 6H), 8.51~8.46 (m, 8H), 8.21~8.14 (m, 6H), 7.87~7.83 (m, 2H), 7.64~7.54 (m, 5H), 1.73 (s, 6H).

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device. N,N-Bis(naphthalene-1-yl)-N,N-bis(phenyl)-benzidine (NPB) is most widely used as the hole transporting layer. 10,10-Dimethyl-12-(4-(pyren-1-yl)phenyl)-10H-indeno[1,2-b]triphenylene (PT-312, US20140175384) is used as blue emitting host and N1,N1,N6,N6-tetramtolylpyrene-1,6-diamine (D1) is used as blue guest. 2-(10,10-dimethyl-10H-indeno[2,1-b]triphenylen-13-yl)-9-phenyl-1,10-phenanthroline is used as electron transporting material (ET1) to co-deposit with 5% Li, 2-(10,10-dimethyl-10H-indeno[2,1-b]triphenylen-12-yl)-4,6-diphenyl-1,3,5-triazine is used as electron transporting material (ET2) to co-deposit with 8-hydroxyquinolato-lithium (LiQ) in organic EL device. Bis(2-methyl-8-quinolinolate)-4-(phenylphenolato)aluminium (BAlq) is used as hole blocking material (HBM) and phosphorescent host for phosphorescent system, Bis(2-phenylpyridinato)(2,4-diphenylpyridinato)iridium(III) (D1) is used as phosphorescent dopant. 4-(10,10-dimethyl-10H-indeno[2,1-b]triphenylen-13-yl)dibenzo[b,d]thiophene (H1) is used as phosphorescent emitting host to co-deposit with the present invention EXAMPLE 1 to 4. The prior art of OLED materials for producing standard organic EL device control and comparable material in this invention shown its chemical structure as following:

HAT-CN

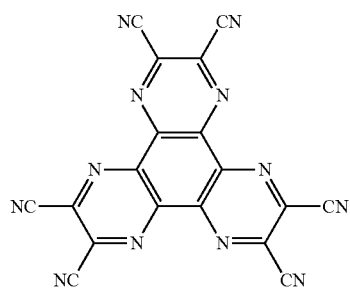

NPB

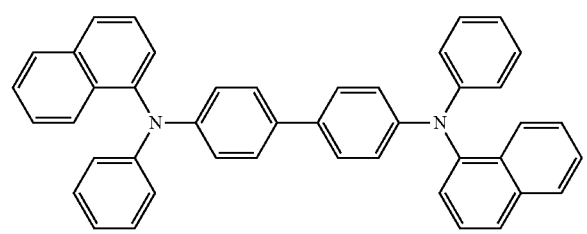

D1

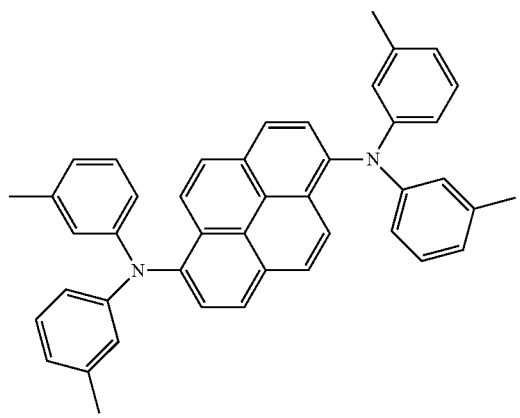

PT-312

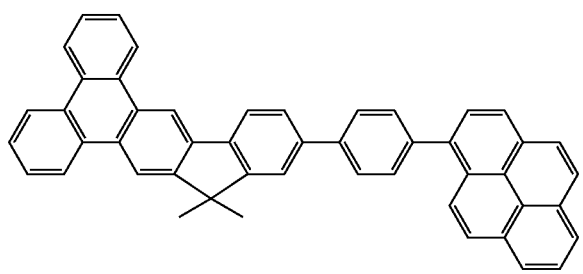

ET1

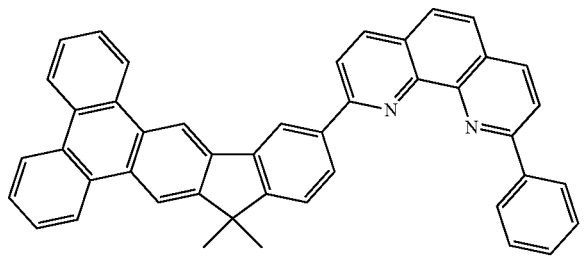

LiQ

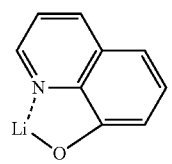

ET2

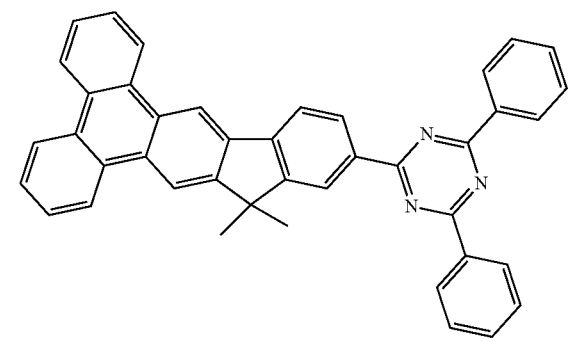

H1
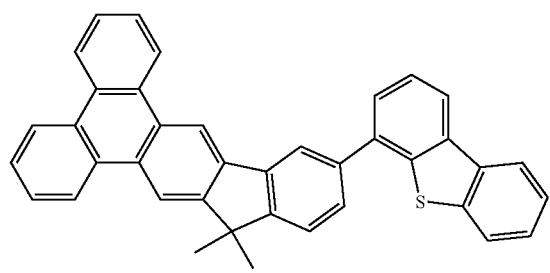
BAlq
D2
EXAMPLE 1
EXAMPLE 2
EXAMPLE 3
EXAMPLE 4

-continued

EXAMPLE 5

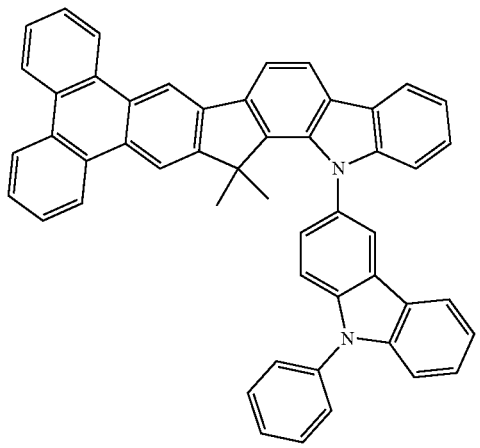

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 6

Using a procedure analogous to the above mentioned general method, fluorescent blue-emitting organic EL device having the following device structure was produced (See FIG. 1): ITO/HAT-CN (20 nm)/NPB (130 nm)/PT-312 doped 5% D1 (30 nm)/HBM (hole blocking material (5 nm)/ET1 co-deposit 5% Li/Al (160 nm). The I-V-B (at 1000 nits) and half-life time of fluorescent blue-emitting organic EL device testing report as Table 1, The half-life time is defined that the initial luminance of 1000 cd/m² has dropped to half.

TABLE 1

| HBM | Voltage (V) | Efficiency (cd/A) | CIE (y) | Half-life time (hour) |
|---|---|---|---|---|
| BAlq | 5.5 | 5.0 | 0.172 | 195 |
| Ex. 1 | 4.5 | 5.6 | 0.181 | 310 |
| Ex. 2 | 4.8 | 5.8 | 0.179 | 300 |
| Ex. 3 | 4.3 | 6.2 | 0.168 | 350 |
| Ex. 4 | 4.5 | 5.6 | 0.169 | 380 |
| Ex. 5 | 5.2 | 5.2 | 0.180 | 260 |

Example 7

Using a procedure analogous to the above mentioned general method, phosphorescent emitting organic EL device having the following device structures are produced (See FIG. 1): ITO/HAT-CN (20 nm)/NPB (130 nm)/phosphorescent host (PHhost)+15% D2 (30 nm)/HBM (15 nm)/ET2 co-deposit LiQ (ET2:LiQ, ratio=1:1) (40 nm)/LiQ (1 nm)/Al (160 nm). The I-V-B (at 1000 nits) and half-life time of phosphorescent emitting organic EL device testing report as Table 1. The half-life time is defined that the initial luminance of 3000 cd/m² has dropped to half.

TABLE 2

| PHhost(H1 + Ex.) H1:Ex. = 1:1 | HBM | Voltage (V) | Efficiency (cd/A) | CIE (x, y) | Half-life time (hour) |
|---|---|---|---|---|---|
| Balq | Balq | 5.8 | 25 | 0.43, 0.56 | 350 |
| H1 + Ex. 1 | — | 4.0 | 38 | 0.42, 0.57 | 560 |
| H1 + Ex. 1 | Ex. 1 | 4.2 | 42 | 0.43, 0.57 | 650 |
| H1 + Ex. 2 | — | 4.2 | 46 | 0.42, 0.58 | 540 |
| H1 + Ex. 3 | Ex. 3 | 4.0 | 39 | 0.44, 0.56 | 760 |
| H1 + Ex. 3 | — | 3.8 | 32 | 0.45, 0.58 | 580 |
| H1 + Ex. 4 | Ex. 4 | 4.0 | 35 | 0.46, 0.55 | 650 |
| H1 + Ex. 4 | Ex. 3 | 3.8 | 32 | 0.46, 0.54 | 580 |
| H1 + Ex. 5 | Ex. 5 | 4.5 | 25 | 0.43, 0.58 | 600 |
| H1 + Ex. 5 | Ex. 3 | 4.5 | 22 | 0.43, 0.57 | 650 |
| Ex. 5 + Ex. 2 | Ex. 3 | 3.5 | 48 | 0.43, 0.56 | 720 |
| Ex. 5 + Ex. 2 | — | 3.6 | 42 | 0.42, 0.56 | 750 |

In the above preferred embodiments for organic EL device test report (see Table 1 and Table 2), we show that the with a general formula (I) and formula (II) in the present invention display good performance than the prior art of OLED materials To sum up, the present invention discloses a compound which can be used for organic EL device is disclosed. More specifically, an organic EL device employing the compound as phosphorescent emitting host, hole blocking layer, or hole blocking electron transport layer. The mentioned compound are represented by the following formula (I) or formula (II):

formula (I)

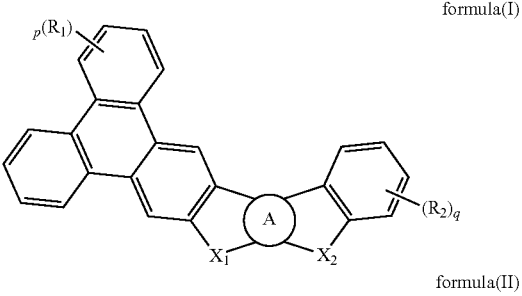

formula (II)

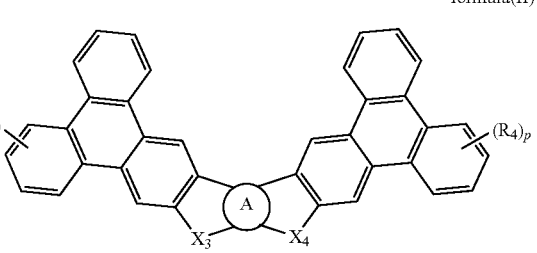

Wherein A represent a substituted or unsubstituted phenyl group, a substituted or unsubstituted naphthyl group. $X_1$ to $X_4$ independently represent a divalent bridge selected from the atom or group consisting from O, S, $C(R_5)(R_6)$, N(Ar), $Si(R_7)$ $(R_8)$. p represent an integer of 0 to 10. q represent an integer of 0 to 4. $R_1$ to $R_8$, and Ar independently selected from the group consisting of a hydrogen atom, a substituted or unsubstituted alkyl group having 1 to 30 carbon atoms, a substituted or unsubstituted aryl group having 6 to 50 carbon atoms, a substituted or unsubstituted aralkyl group having 6 to 50 carbon atoms, a substituted or unsubstituted heteroaryl group having 3 to 50 carbon atoms.

The invention claimed is:

1. A compound with a general formula (I) or formula (II) as following:

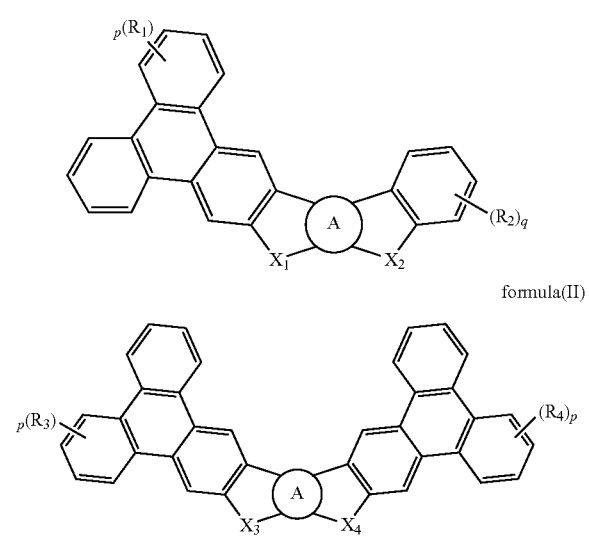

formula(I)

formula(II)

Wherein A represent a substituted or unsubstituted phenyl group, a substituted or unsubstituted naphthyl group. $X_1$ to $X_4$ independently represent a divalent bridge selected from the atom or group consisting from O, S, C($R_5$)($R_6$), N(Ar), Si($R_7$)($R_8$). p represent an integer of 0 to 10. q represent an integer of 0 to 4. $R_1$ to $R_8$, and Ar independently selected from the group consisting of a hydrogen atom, a substituted or unsubstituted alkyl group having 1 to 30 carbon atoms, a substituted or unsubstituted aryl group having 6 to 50 carbon atoms, a substituted or unsubstituted aralkyl group having 6 to 50 carbon atoms, a substituted or unsubstituted heteroaryl group having 3 to 50 carbon atoms.

2. According to claim 1, wherein the compound is represented the following formula (I-1) to formula (I-4) or formula (II-1) to formula (II-4):

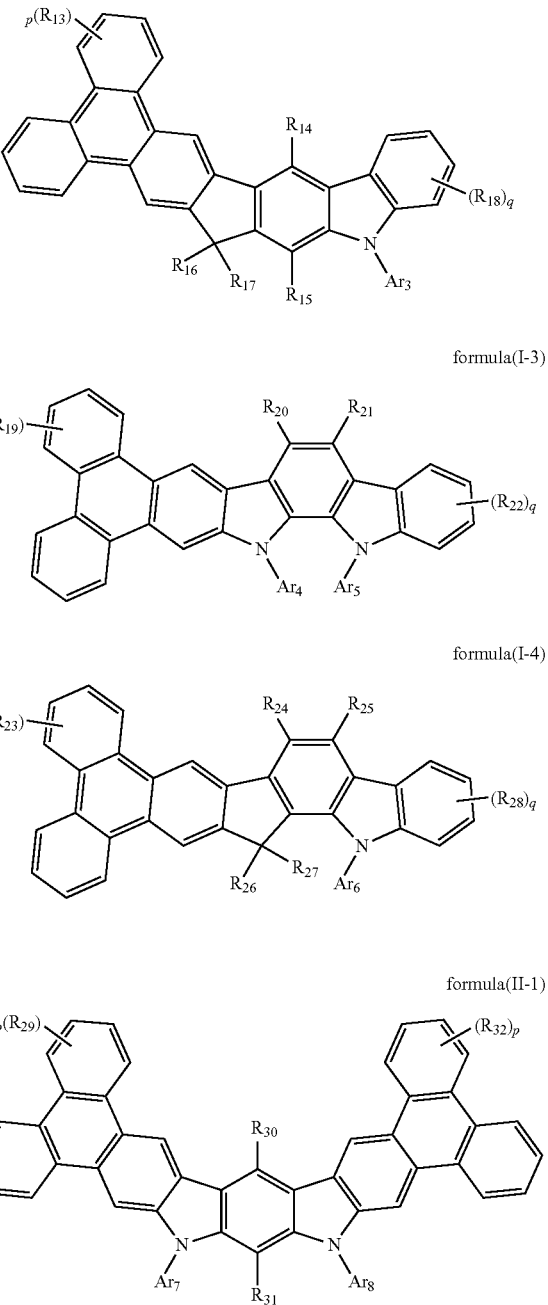

-continued

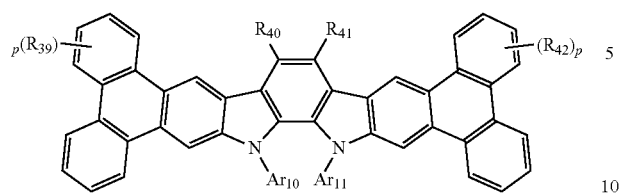
formula(II-3)

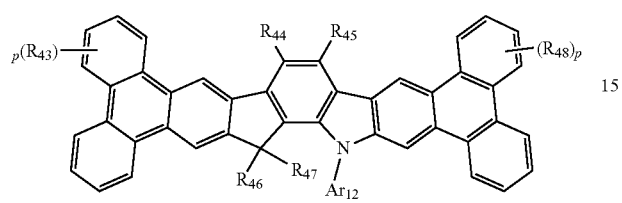
formula(II-4)

wherein $R_9$ to $R_{48}$ are the same definition as $R_1$, and p, q are same definition as described the above-mentioned formula (I) and formula (II), $Ar_1$ to $Ar_{12}$ is represented by the following formula (III):

formula(III)

wherein L represent a single bond, a substituted or unsubstituted arylene group having 6 to 30 ring carbon atoms, or a substituted or unsubstituted heterarylene group having 3 to 30 ring carbon atoms. Y represent a substituted or unsubstituted phenyl group, a substituted or unsubstituted naphthyl group, a substituted or unsubstituted biphenyl group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted phenanthroline group, a substituted or unsubstituted dihydroacridine group, a substituted or unsubstituted phenothiazine group, a substituted or unsubstituted phenoxazine group, a substituted or unsubstituted dihydrophenazine group.

3. According to claim 2, the formula (III) for L are consisting of group represent as following:

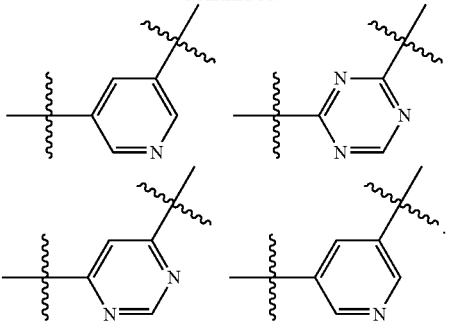

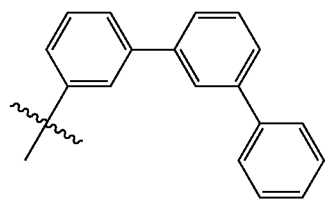

4. According to claim 2, the formula (III) for Y are consisting of group represent as following:

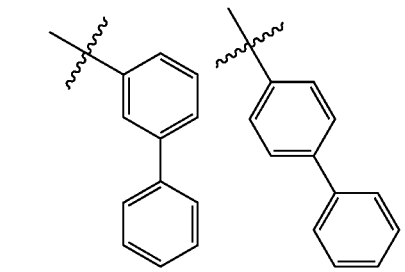

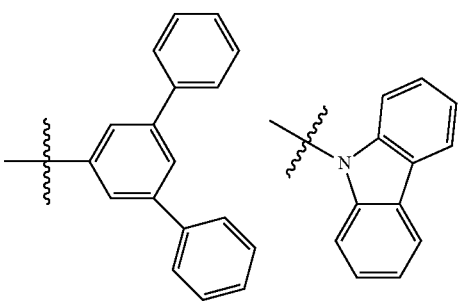

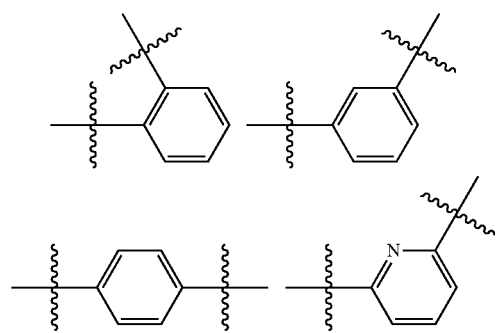

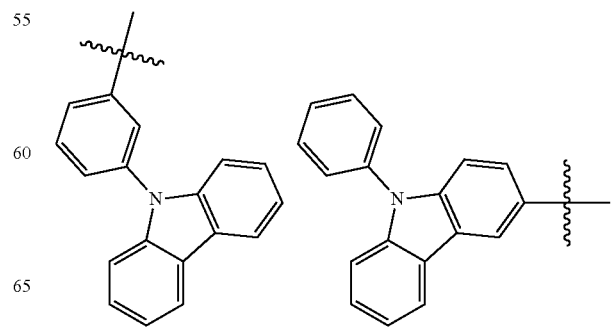

51
-continued
52
-continued
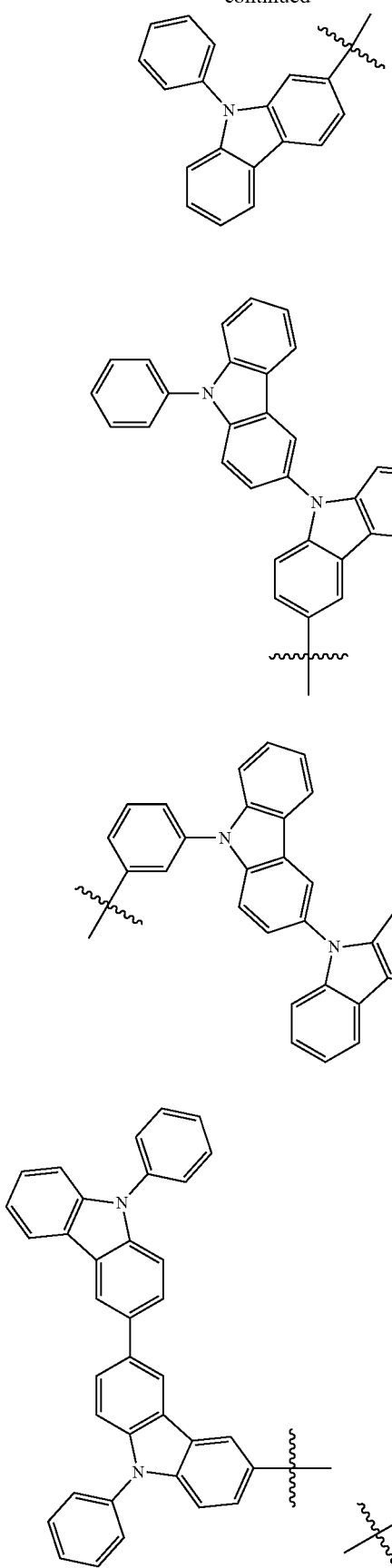

53
-continued

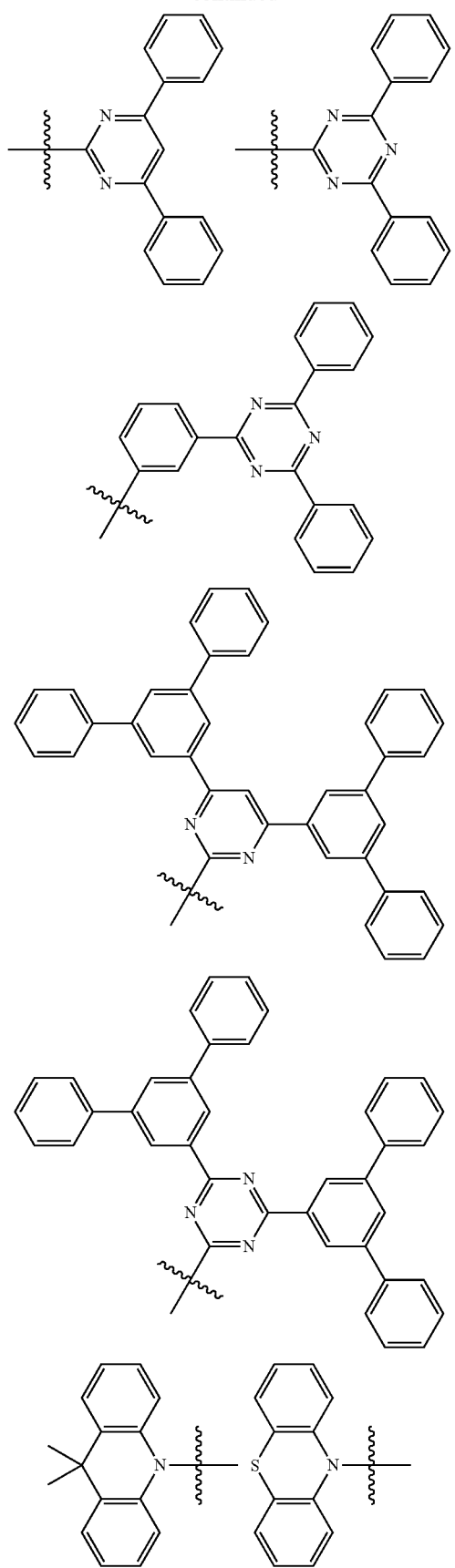

54
-continued

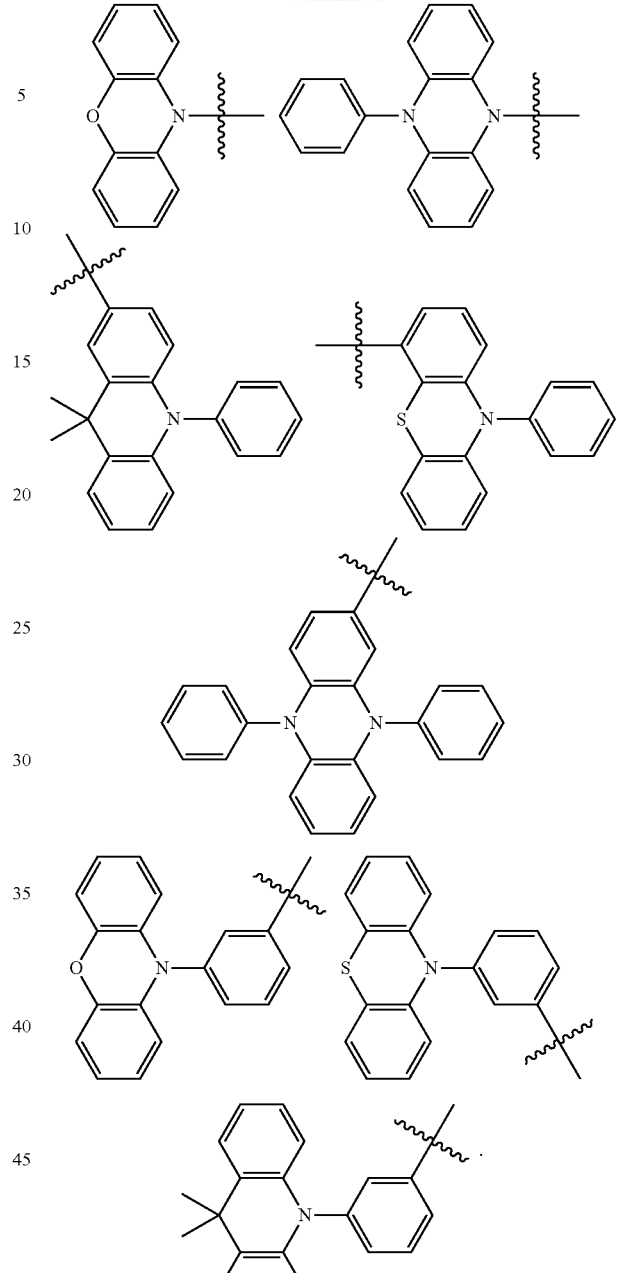

5. A organic electroluminescent device comprising a pair of electrodes consisting of a cathode and an anode and between the pairs of electrodes comprising at least a layer of the compound with a general formula (I) or formula (II) according to claim 1.

6. The organic electroluminescent device according to claim 5, wherein the emitting layer comprising the compound with a general formula (I) or formula (II).

7. The organic electroluminescent device according to claim 6, wherein the emitting layer comprising the compound with a general formula (I) or formula (II) is a phosphorescent host material, or a thermally activated delayed fluorescence host material.

8. The organic electroluminescent device according to claim 6, wherein the emitting layer comprising phosphorescent dopant or thermally activated delayed fluorescence dopant.

9. The organic electroluminescent device according to claim 8, wherein the phosphorescent dopant are iridium (Ir) complexes.

10. The organic electroluminescent device according to claim 5, wherein the hole blocking layer comprising the compound with a general formula (I) or formula (II).

11. The organic electroluminescent device according to claim 5, wherein the hole blocking electron transport layer comprising the compound with a general formula (I) or formula (II).

12. The organic electroluminescent device according to claim 5, wherein the emitting layer comprising compound as the following:

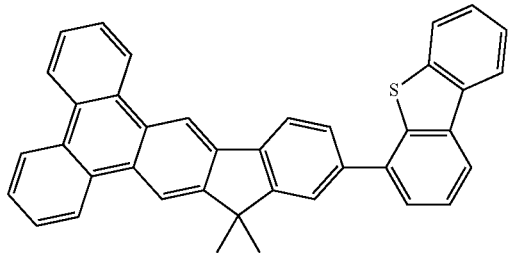

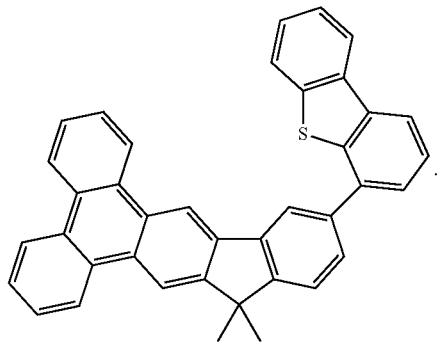

13. The organic electroluminescent device according to claim 5, wherein the electron transport layer comprising compounds as the following:

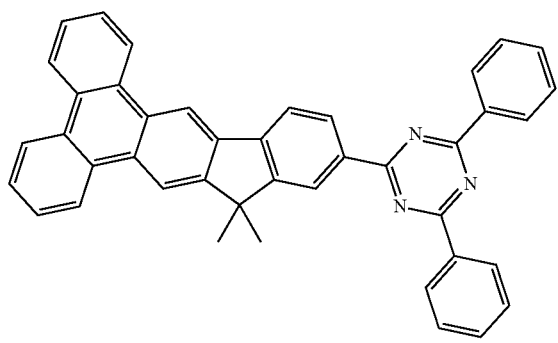

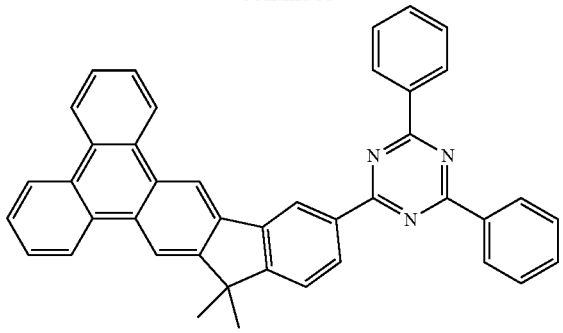

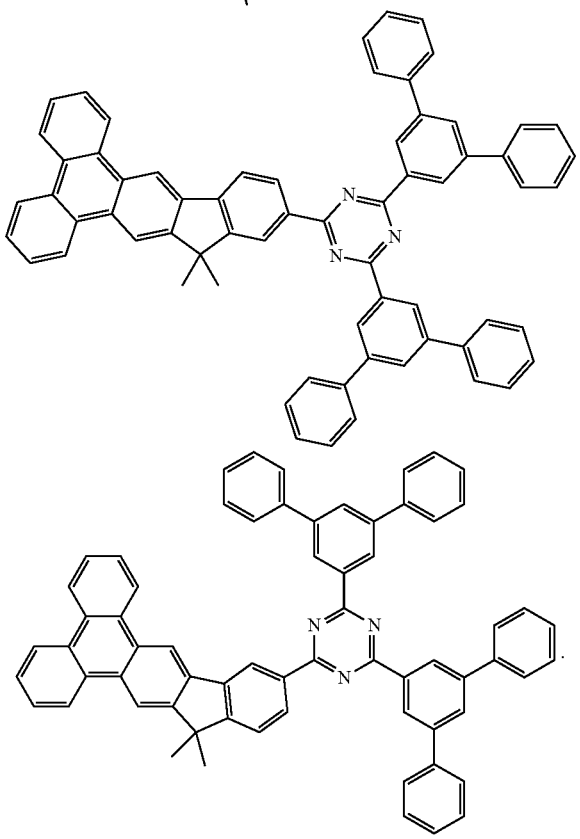

14. The organic electroluminescent device according to claim 13, wherein the electron transport layer comprising lithium or 8-hydroxyuinolinolato-lithium.

15. According to claim 1, the compound with a general formula (I) or formula (II) are

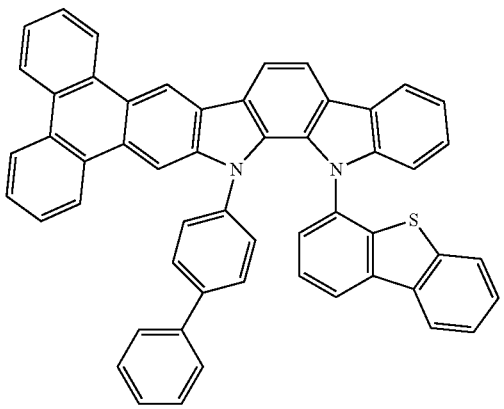

57
-continued
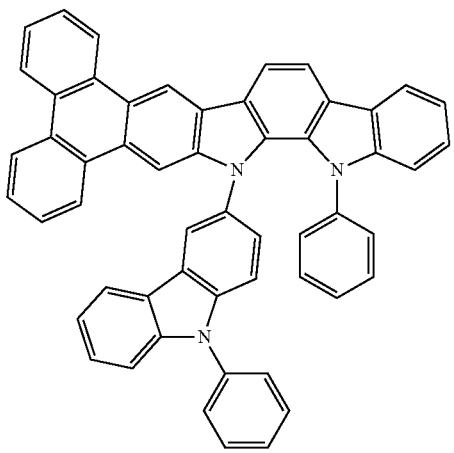
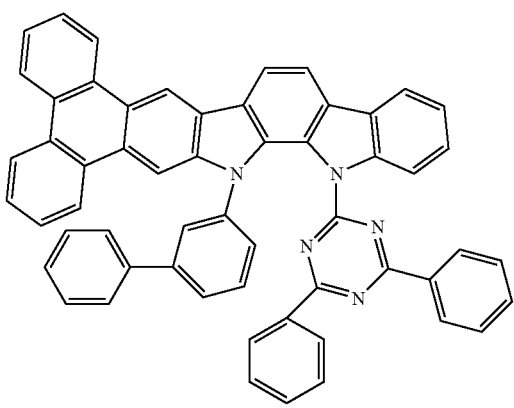
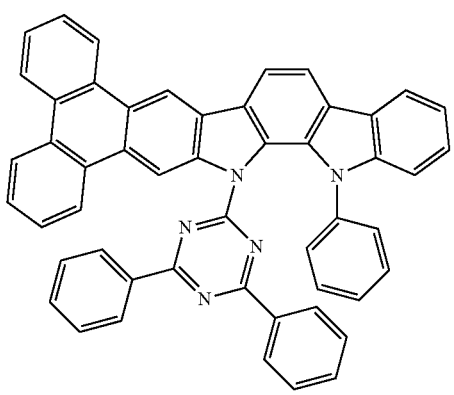
58
-continued
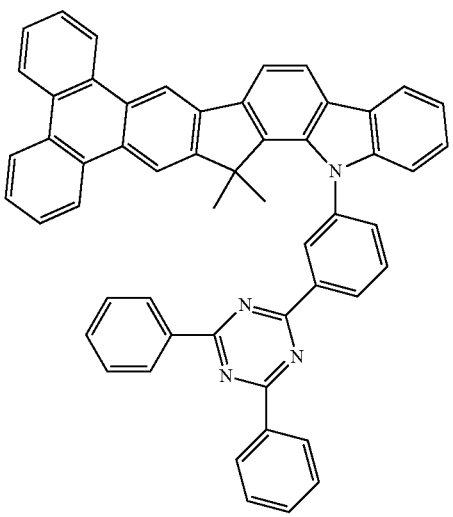
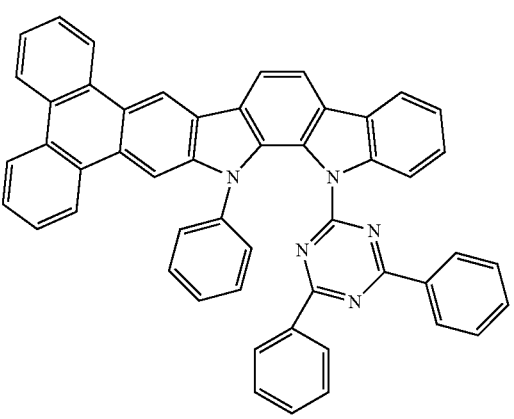
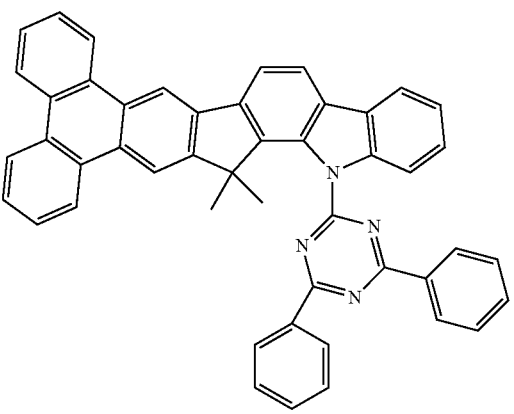

59
-continued
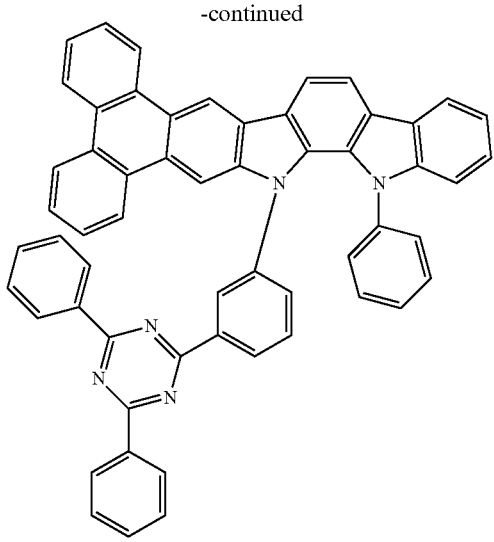
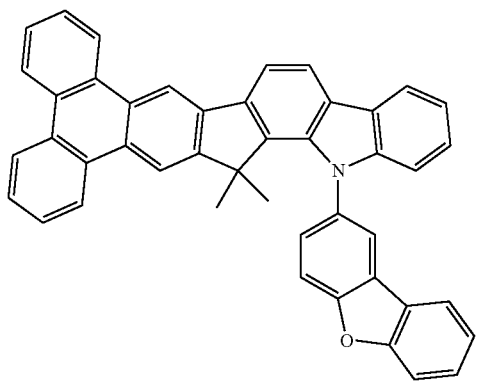
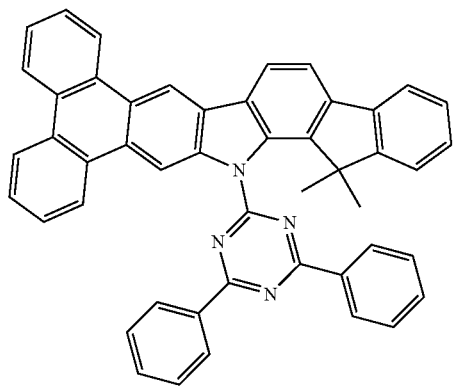
60
-continued
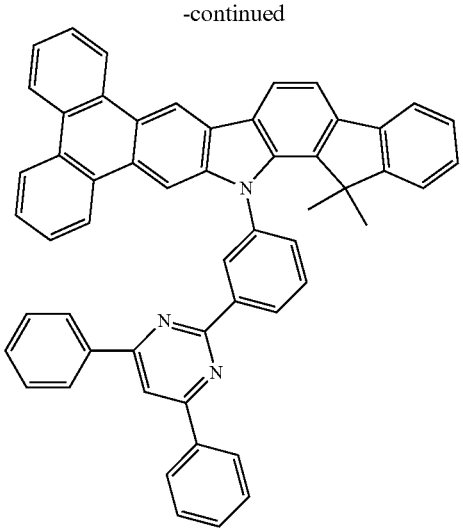
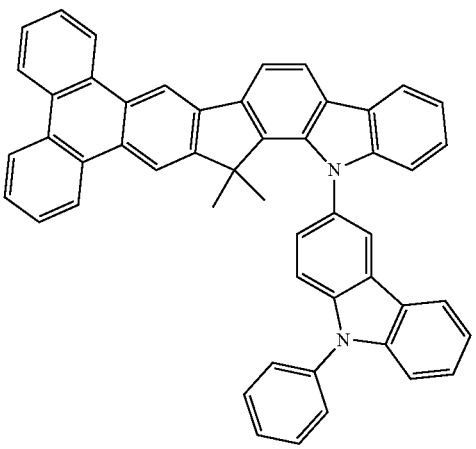
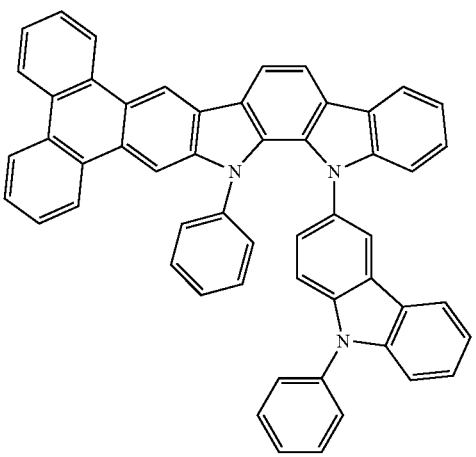

61
62
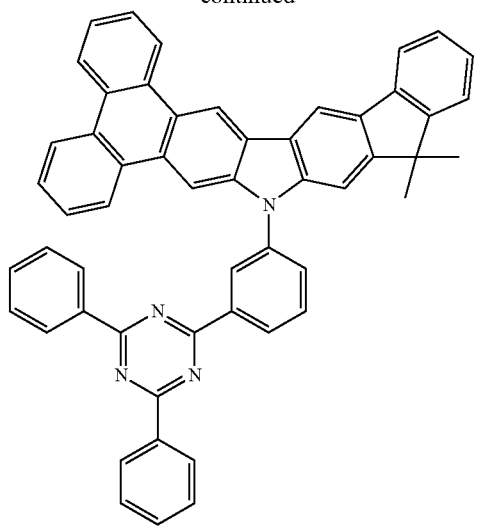
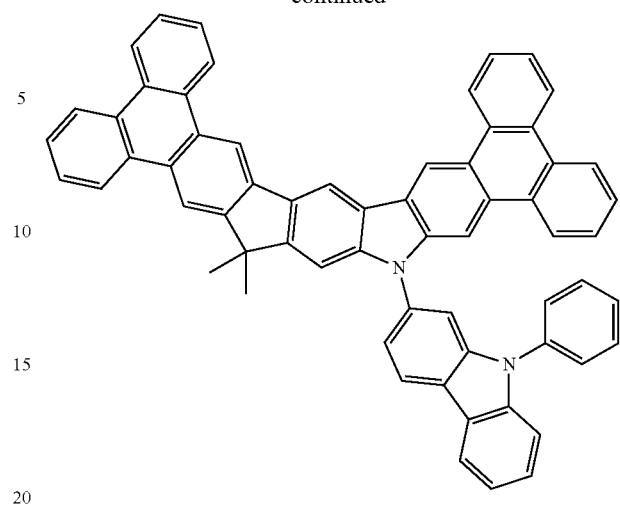
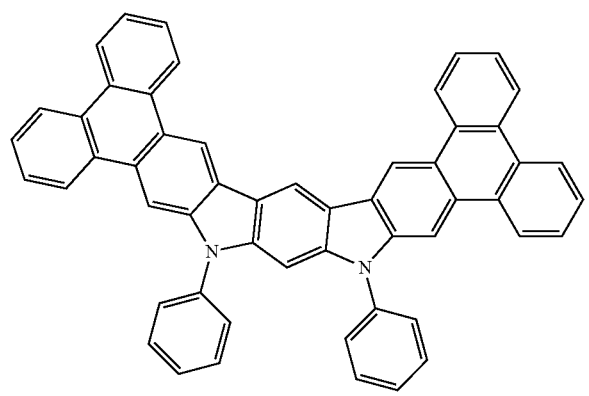
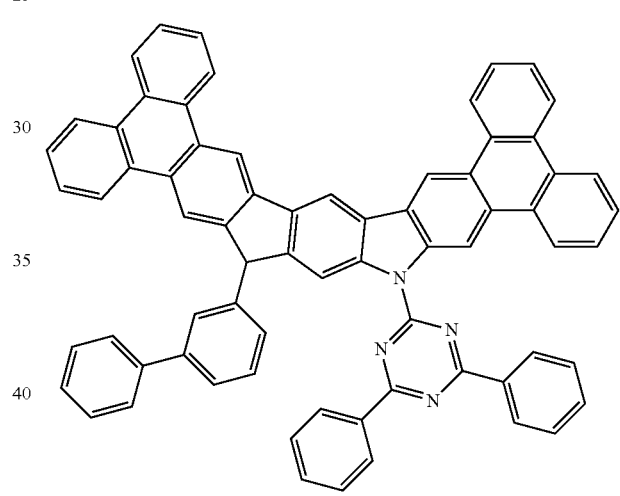
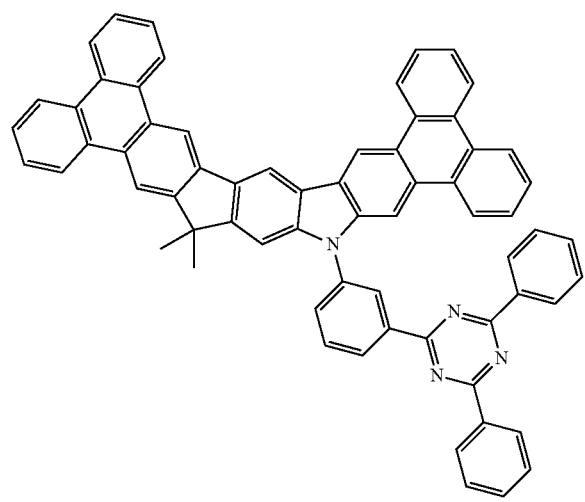
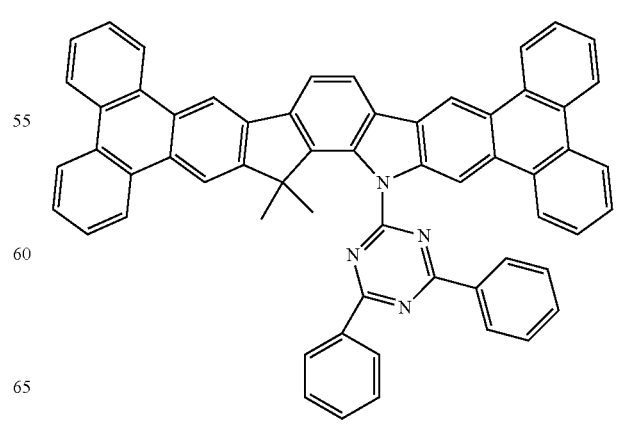

63
-continued
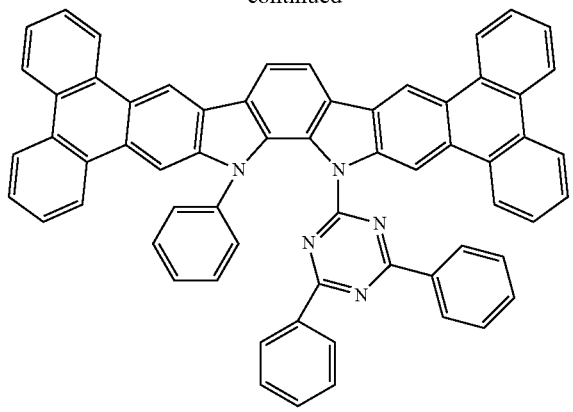
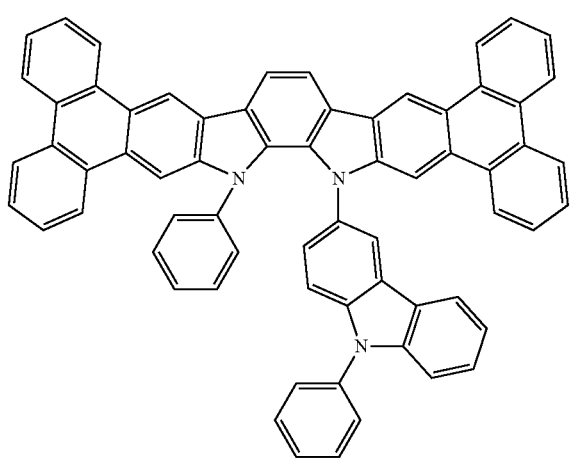
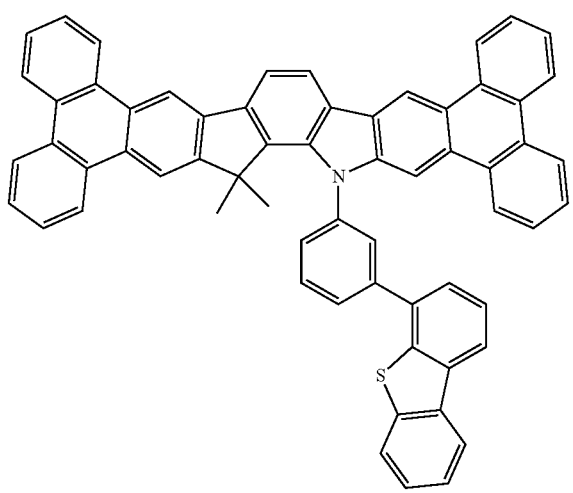
64
-continued
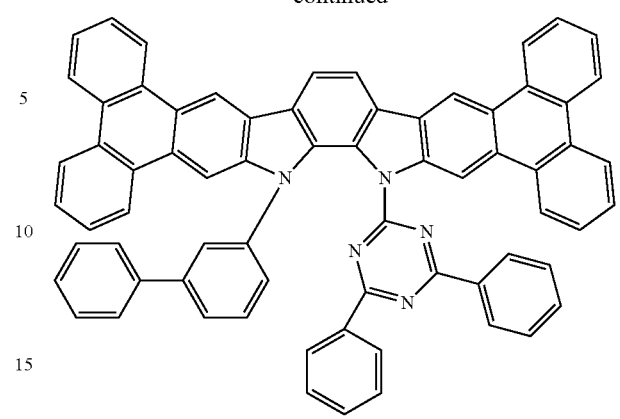
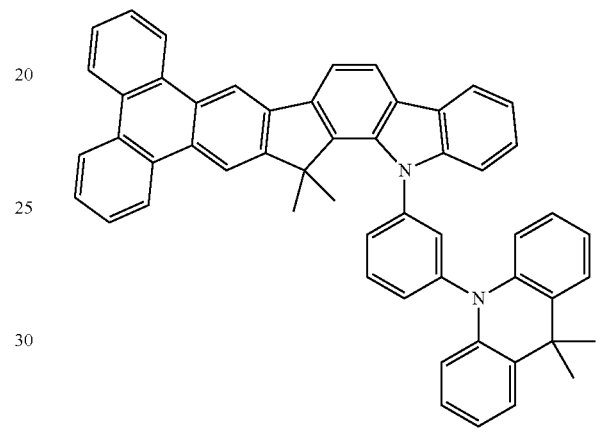
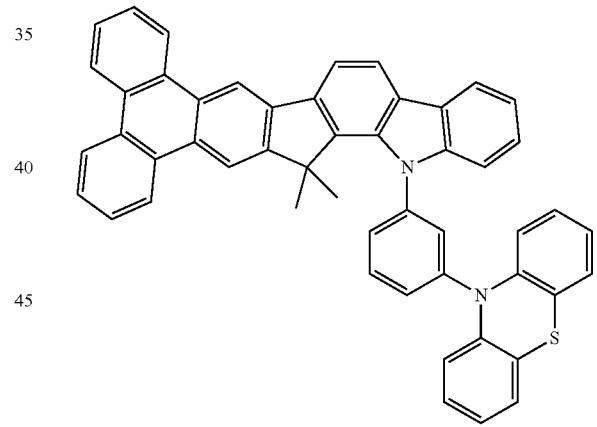
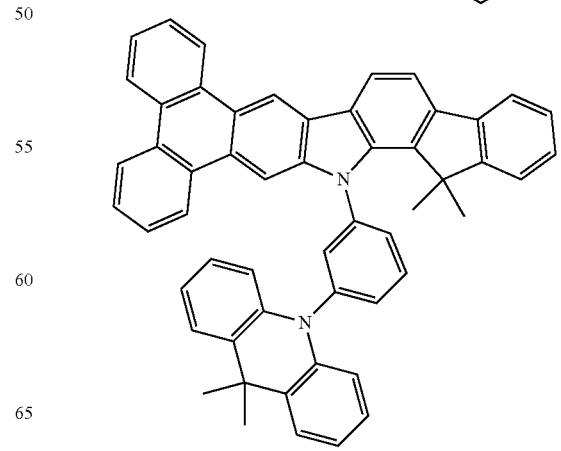

65
-continued
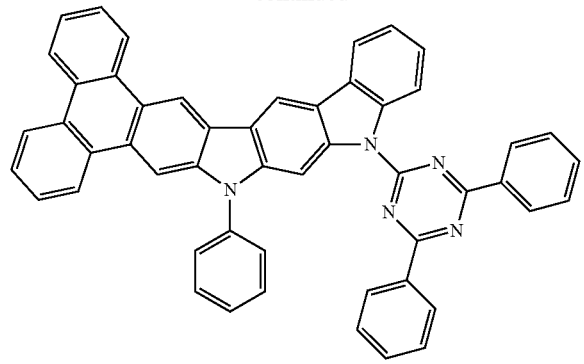
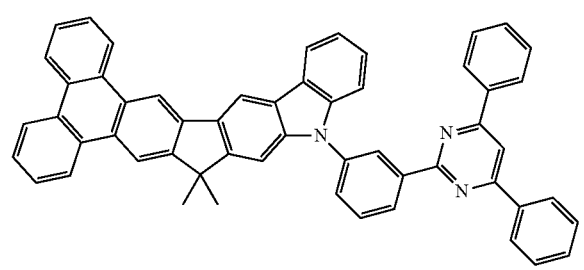
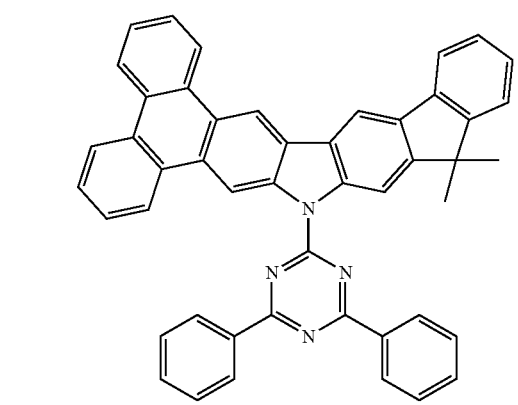
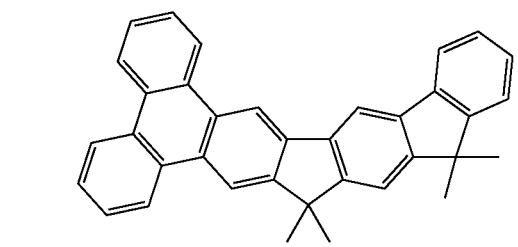
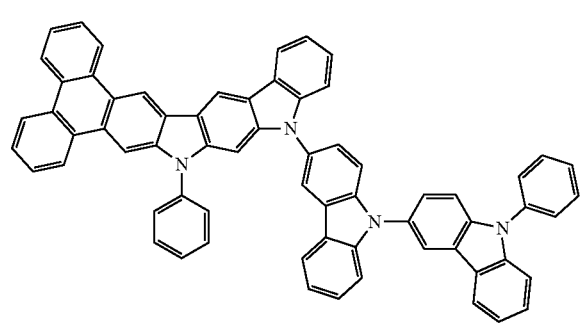
66
-continued
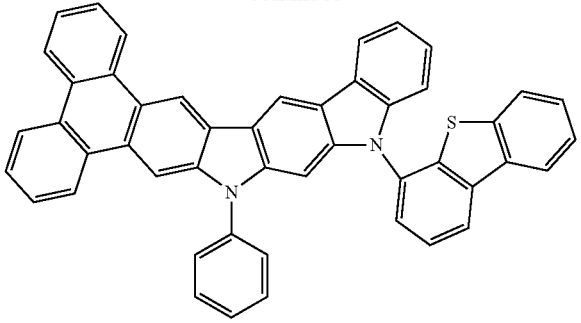
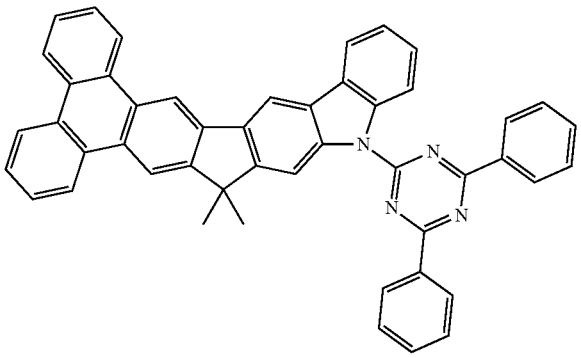
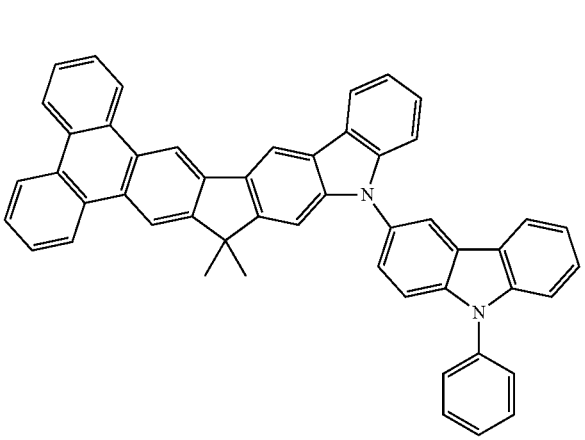
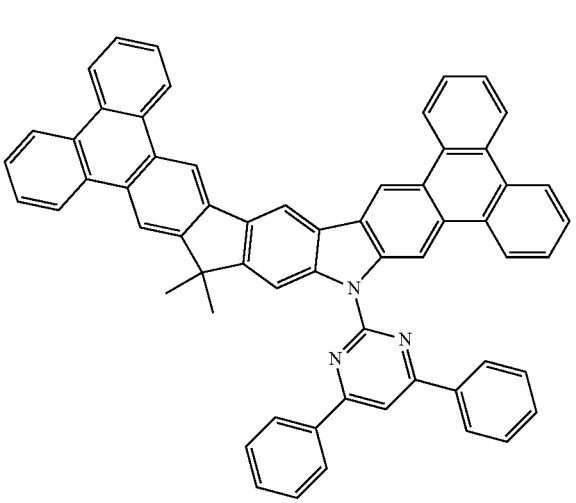

67
-continued
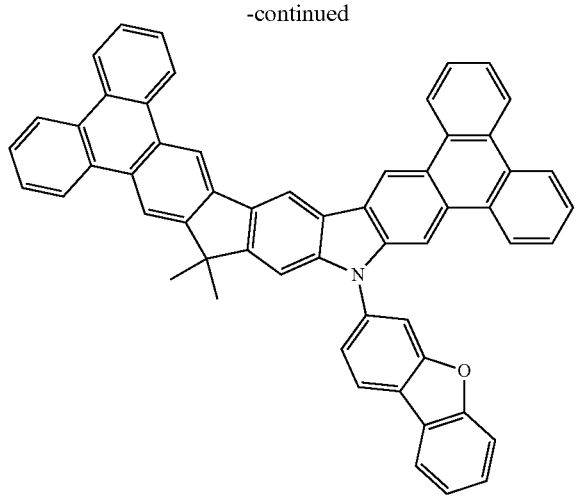
68
-continued
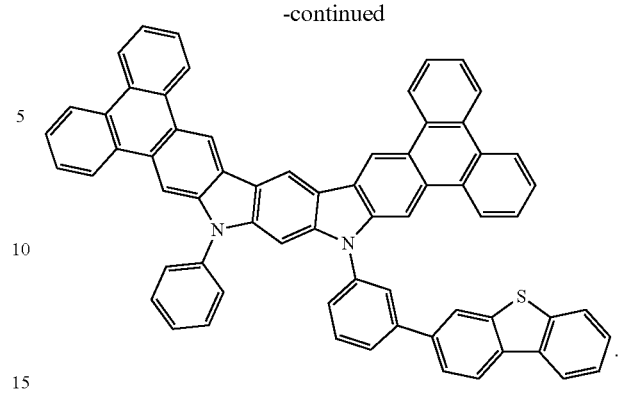
* * * * *